US012765577B2

(12) United States Patent
Friesen et al.

(10) Patent No.: US 12,765,577 B2
(45) Date of Patent: Oct. 20, 2026

(54) FEED ADDITIVE COMPOSITIONS

(71) Applicant: ELANCO US INC., Greenfield, IN (US)

(72) Inventors: Kim Friesen, Carthage, IN (US); Chester Wiernusz, Canton, GA (US); Ryan Cooney, Mankato, MN (US)

(73) Assignee: ELANCO US INC., Indianapolis, IN (US)

( * ) Notice: Subject to any disclaimer, the term of this patent is extended or adjusted under 35 U.S.C. 154(b) by 0 days.

(21) Appl. No.: 17/809,332

(22) Filed: Jun. 28, 2022

(65) Prior Publication Data

US 2022/0338504 A1 Oct. 27, 2022

Related U.S. Application Data

(63) Continuation of application No. 16/195,242, filed on Nov. 19, 2018, now abandoned.

(60) Provisional application No. 62/587,860, filed on Nov. 17, 2017.

(51) Int. Cl.

| | |
|---|---|
| ***A23K 10/18*** | (2016.01) |
| ***A23K 10/30*** | (2016.01) |
| ***A23K 20/10*** | (2016.01) |
| ***A23K 20/142*** | (2016.01) |
| ***A23K 20/158*** | (2016.01) |
| ***A23K 20/163*** | (2016.01) |
| ***A23K 20/195*** | (2016.01) |
| ***A23K 20/20*** | (2016.01) |
| ***A23K 50/75*** | (2016.01) |
| ***A61K 33/00*** | (2006.01) |
| ***A61K 35/742*** | (2015.01) |
| ***A61K 36/06*** | (2006.01) |
| ***A61K 36/81*** | (2006.01) |
| ***A61K 45/06*** | (2006.01) |

(52) U.S. Cl.

CPC .............. *A23K 10/18* (2016.05); *A23K 10/30* (2016.05); *A23K 20/10* (2016.05); *A23K 20/142* (2016.05); *A23K 20/158* (2016.05); *A23K 20/163* (2016.05); *A23K 20/195* (2016.05); *A23K 20/20* (2016.05); *A23K 50/75* (2016.05); *A61K 33/00* (2013.01); *A61K 35/742* (2013.01); *A61K 36/06* (2013.01); *A61K 36/81* (2013.01); *A61K 45/06* (2013.01)

(58) Field of Classification Search

None

See application file for complete search history.

(56) References Cited

U.S. PATENT DOCUMENTS

| | | | | |
|---|---|---|---|---|
| 2012/0244191 | A1* | 9/2012 | Skinner ................ | A61K 36/064 424/269.1 |
| 2017/0095508 | A1* | 4/2017 | Hagen ..................... | A61K 33/26 |
| 2017/0246222 | A1* | 8/2017 | Lewis ..................... | A61K 35/74 |

FOREIGN PATENT DOCUMENTS

WO WO-2017173393 A1 * 10/2017

OTHER PUBLICATIONS

Gadde et al., "Alternatives to antibiotics for maximizing growth performance and feed efficiency in poultry: a review", Animal Health Research Reviews, vol. 18, pp. 26-45 (e-Publication: May 2017) (Year: 2017).*

Lillehoj et al., "Effects of dietary plant-derived phytonutrients on the genome-wide profiles and coccidiosis resistance in the broiler chickens", BMC Proceedings, vol. 5, Article S34, pp. 1-8 (Year: 2011).*

* cited by examiner

*Primary Examiner* — Michelle F. Paguio Frising

(74) *Attorney, Agent, or Firm* — Barnes & Thornburg LLP

(57) ABSTRACT

The present invention provides feed compositions comprising a basal animal diet supplemented with direct fed microbial (DFM) and at least one of a formulated yeast, a *Capsicum* product, and an antimicrobial clay. The feed compositions improve growth, general health, intestinal health, and reduce microbial pathogens in non-human animals fed the feed compositions.

19 Claims, No Drawings

FEED ADDITIVE COMPOSITIONS

CROSS-REFERENCE TO RELATED APPLICATIONS

This application claims priority to U.S. Non-Provisional Patent application Ser. No. 16/195,242 filed Nov. 19, 2018, which claims the benefit of U.S. Provisional Patent Application No. 62/587,860 filed Nov. 17, 2017, the entire disclosure of which is incorporated herein by reference.

FIELD OF THE INVENTION

The present disclosure generally relates to feed additive compositions, methods for improving growth, improving health, improving intestinal health, and the reduction of microbial pathogens in non-human animals.

BACKGROUND OF THE INVENTION

Animal husbandry is a branch of agriculture concerned with raising, breeding, and day to day care of animals. Farmers engaged in this branch of agriculture produce meat, eggs, milk, and other products for the consumer. Additionally, these farmers are engaged in breeding and raising a wide variety of animals.

Farmers engaged in animal husbandry face many challenges. The demand for food and food products from animal husbandry is anticipated to increase significantly as the population is growing. Also, with the increase in population, increased demands on land, water, and energy resources are being realized. Global environmental challenges, including global climate changes and the growing threat of disease transmission to and from agricultural animals, add further challenges. Therefore, farmers need to become more efficient, produce the products at a higher rate, and raise livestock and poultry at an increased rate to meet market challenges. Additionally, farmers need a low cost method to produce these products since the profit margin in these areas can be quite low.

In the past, farmers used antibiotics and hormones to not only control diseases and pathogens but also to promote growth in livestock and poultry. Due to changes in consumer sentiment towards the use of antibiotics, there is an increase of production that is reared without the use of antibiotics.

To meet these challenges, what is needed is a feed additive which is generally low cost but also promotes health, growth, and reduces the levels of pathogens in animals without having to use antibiotics and hormones.

SUMMARY OF THE INVENTION

In one aspect, the present disclosure provides a feed composition for non-human animals. The composition comprises a basal animal diet supplemented with a combination of active ingredients selected from *Capsicum* product and a DFM; antimicrobial clay and a DFM; formulated yeast and a DFM; *Capsicum* product, formulated yeast, and a DFM, and *Capsicum* product and formulated yeast.

The DFM may be *Bacillus licheniformis.* When the the DFM is *Bacillus licheniformis,* the *Bacillus licheniformis* in the feed composition may be at a concentration of about $1\times10^4$ cfu/g to about $1\times10^6$ cfu/g feed.

The *Capsicum* product in the feed composition may be at a concentration of about 0.1 lb/ton to about 0.5 lb/ton feed. The *Capsicum* product may be selected from the group consisting of a capsaicinoid, a vanilloid, *Capsicum,* macerated hot peppers, ground hot peppers, hot pepper extract, capsaicin-containing plant materials, encapsulated ground peppers, a coated capsaicin product, and combinations of any thereof. In some embodiments, the *Capsicum* product is encapsulated ground peppers. When the *Capsicum* product is encapsulated ground peppers, the *Capsicum* product comprises about 45% to about 55% ground peppers and/or comprises about 0.4% to about 0.6% capsaicinoids.

The formulated yeast may comprise about 80-100% yeast extract. When the formulated yeast comprises yeast extract, the formulated yeast in the feed composition may be at a concentration of about 0.3 lb/ton of feed to about 0.7 lb/ton of feed. The antimicrobial clay may be mined clay. When the antimicrobial clay is mined clay, the clay in the feed composition is at a concentration of about 2 to about 6 lb/ton feed.

In some embodiments, the composition comprises formulated yeast, *Capsicum* product, and DFM. In an alternative of the embodiments, the DFM is *Bacillus licheniformis.* In an alternative of the embodiments wherein the DFM is *Bacillus licheniformis,* the formulated yeast in the feed composition is at a concentration of about 0.3 lb/ton to about 0.7 lb/ton feed, the *Capsicum* product in the feed composition is at a concentration of about 0.1 lb/ton to about 0.5 lb/ton feed, and the *Bacillus licheniformis* in the feed composition is at a concentration of about $1\times10^4$ cfu/g to about $1\times10^6$ cfu/g feed.

In other embodiments, the composition comprises *Capsicum* product and DFM. In an alternative of the embodiments, the DFM is *Bacillus licheniformis.* In an alternative of the embodiments wherein the DFM is *Bacillus licheniformis,* the *Capsicum* product in the feed composition is at a concentration of about 0.1 lb/ton to about 0.5 lb/ton feed and the *Bacillus licheniformis* in the feed composition is at a concentration of about $1\times10^4$ cfu/g to about $1\times10^6$ cfu/g feed.

In yet other embodiments, the composition comprises antimicrobial clay and DFM. In an alternative of the embodiments, the DFM is *Bacillus licheniformis.* In an alternative of the embodiments wherein the DFM is *Bacillus licheniformis,* the antimicrobial clay in the feed composition is at a concentration of about 2 lb/ton to about 6 lb/ton feed and the *Bacillus licheniformis* in the feed composition is at a concentration of about $1\times10^4$ cfu/g to about $1\times10^6$ cfu/g feed.

In other embodiments, the composition comprises formulated yeast, and DFM. In an alternative of the embodiments, the DFM is *Bacillus licheniformis.* In an alternative of the embodiments wherein the DFM is *Bacillus licheniformis,* the formulated yeast in the feed composition is at a concentration of about 0.3 lb/ton to about 0.7 lb/ton feed, and the *Bacillus licheniformis* in the feed composition is at a concentration of about $1\times10^4$ cfu/g to about $1\times10^6$ cfu/g feed.

In additional embodiments, the composition comprises formulated yeast, and *Capsicum* product. In an alternative of the embodiments, the formulated yeast in the feed composition is at a concentration of about 0.3 lb/ton to about 0.7 lb/ton feed, and the *Capsicum* product in the feed composition is at a concentration of about 0.1 lb/ton to about 0.5 lb/ton feed.

In other aspects, the present disclosure provides a feed composition for non-human animals comprising a basal animal diet supplemented with *Capsicum* product and *Bacillus licheniformis;* a feed composition for non-human animals comprising a basal animal diet supplemented with antimicrobial clay and *Bacillus licheniformis;* a feed composition for non-human animals comprising a basal animal diet supplemented with formulated yeast and *Bacillus licheniformis;* a feed composition for non-human animals comprising a basal animal diet supplemented with *Capsicum* product, formulated yeast, and *Bacillus licheniformis;* or a feed composition for non-human animals comprising a basal animal diet supplemented with *Capsicum* product and formulated yeast.

In another aspect, the present disclosure provides a method for improving health in non-human animals, the method comprising feeding the non-human animal the feed composition described above. Improving the health of a non-human animal may be selected from reducing incidence of diarrhea, reducing number of days of diarrhea, decreasing mortality, improving intestinal health, reducing microbial pathogens in the intestinal tract of the animal, decreasing cytokine panel measuring TNF-alpha, and combinations thereof. Further, the non-human animal may be a chicken. When the non-human animal is a chicken, improving the health of the chicken comprises reducing the impact of *C. perfringens* in broilers.

In yet another aspect, the present disclosure provides a method for improving performance of non-human animals, the method comprising feeding the non-human animal the feed composition described above. Improving performance may be selected from increase in body weight gain, feed conversion rate (FCR), feed intake, average daily weight gain (ADG), an increase in average daily food intake (ADFI), an improved overall body weight, and ratio of F/G. The non-human animal may be a chicken.

In yet another aspect, the present disclosure provides method for improving quality of a product derived from a non-human animal, the method comprising feeding the non-human animal the feed composition described above. Improving the quality of a product derived from a non-human animal may be selected from from improving breast meat yield, reducing product variability, reducing impact on consumer appeal due to poor color, poor texture, and drip loss in retail display, reducing organoleptic qualities in cooked chicken, including incidence of woody breast. The non-human animal may be a chicken.

DETAILED DESCRIPTION OF THE INVENTION

The present disclosure is based on the discovery that administering to non-human animals a feed composition comprising at least two active ingredients selected from a direct fed microbial (DFM), a formulated yeast, a *Capsicum* product, and an antimicrobial clay increases animal production, improves animal health, and/or improves performance. As such, the instant invention is directed generally to basal animal diets supplemented with at least two active ingredients selected from a direct fed microbial (DFM), a formulated yeast, a *Capsicum* product, and an antimicrobial clay, and methods of using the feed compositions. For instance, feed compositions may be used to improve the health of a non-human animal. Additionally, feed compositions may be administered to animals to improve mortality, growth performance and feed conversion, and improve the quality of products from animals.

(I) Feed Compositions

One aspect of the present disclosure encompasses feed compositions for non-human animals. The compositions comprise a basal animal diet supplemented with at least two active ingredients selected from a direct fed microbial (DFM), a formulated yeast, a *Capsicum* product, and an antimicrobial clay. In some embodiments, feed compositions comprise a basal animal diet supplemented with *Capsicum* product and a DFM. In other embodiments, feed compositions comprise a basal animal diet supplemented with antimicrobial clay and a DFM. In yet other embodiments, feed compositions comprise a basal animal diet supplemented with formulated yeast and a DFM. In additional embodiments, feed compositions comprise a basal animal diet supplemented with *Capsicum* product, formulated yeast, and a DFM. In some embodiments, feed compositions comprise a basal animal diet supplemented with *Capsicum* product and formulated yeast.

(a) Direct Fed Microbial

As used herein, the term "direct fed microbial" (DFM) is used to refer to a probiotic or prebiotic living microorganisms that provide health benefits when ingested by an animal. DFMs may include yeast, bacteria, and combinations thereof.

By way of non-limiting example, yeast DFMs may comprise *Saccharomyces bisporus, Saccharomyces boulardii, Saccharomyces cerevisiae, Saccharomyces capsularis, Saccharomyces delbrueckii, Saccharomyces fermentati, Saccharomyces lugwigii, Saccharomyces microellipsoides, Saccharomyces pastorianus, Saccharomyces rosei, Candida albicans, Candida cloaceae, Candida tropicalis, Candida utilis, Geotrichum candidum, Hansenula americana, Hansenula anomala, Hansenula wingei,* and *Aspergillus oryzae.*

Non-limiting examples of bacterial DFMs include *Lactobacillus acidophilus, Bifidobacterium thermophilum, Bifidobacterium longhum, Streptococcus faecium, Bacillus pumilus, Bacillus subtilis, Bacillus licheniformis, Lactobacillus casei, Enterococcus faecium, Bifidobacterium bifidium, Propionibacterium acidipropionici, Propionibacterium freudenreichii, and Bifdobacterium pscudologum.*

The amount of DFM in a feed composition can and will vary depending on the DFM, the type of non-human animal that will be administered the feed composition, the body weight, sex, and medical condition of the non-human animal among other variables, and can be determined experimentally. Preferably, a DFM suitable for feed compositions of the disclosure is *Bacillus licheniformis.* When a DFM of a feed composition is *Bacillus licheniformis,* the concentration of *Bacillus licheniformis* in the feed composition may range from about $1\times10^1$ cfu/g of feed to about $1\times10^{10}$ cfu/g of feed, from about $1\times10^1$ cfu/g of feed to about $1\times10^6$ cfu/g of feed, from about $1\times10^5$ cfu/g of feed to about $1\times10^{10}$ cfu/g of feed, or from about $1\times10^3$ cfu/g of feed to about $1\times10^8$ cfu/g of feed. Preferably, the concentration of *Bacillus licheniformis* is about $1\times10^4$ to about $1\times10^6$ cfu/g feed.

(b) Formulated Yeast

As used herein, the formulated yeast product may comprise a combination of *Saccharomyces cerevisiae* yeast extract representing approximately 25-100% of the total formulated yeast product by weight, hydrolyzed yeast representing approximately 0-40% of the total formulated yeast product by weight, a yeast culture representing approximately 0-50% of the total formulated yeast product by weight. The formulated yeast may also comprise limestone representing approximately 0-50% of the total formulated yeast product by weight.

The formulated yeast may be any yeast provided the yeast is generally regarded as safe for use in food or medical applications. Non-limiting examples of formulated yeast-derived products may include yeast cell wall derived components such as β-glucans, arabinoxylan isomaltose, agarooligosaccharides, lactosucrose, cyclodextrins, lactose, fructooligosaccharides, laminariheptaose, lactulose, β-galactooligosaccharides, mannanoligosaccharides, raffinose, stachyose, oligofructose, glucosyl sucrose, sucrose thermal oligosaccharide, isomalturose, caramel, inulin, and xylooligosaccharides. In an embodiment, the formulated yeast may be β-glucans and/or mannanoligosaccharides. Sources for yeast cell wall derived components include *Saccharomyces bisporus, Saccharomyces boulardii, Saccharomyces cerevisiae, Saccharomyces capsularis, Saccharomyces delbrueckii, Saccharomyces fermentati, Saccharomyces lugwigii, Saccharomyces microellipsoides, Saccharomyces pastorianus, Saccharomyces rosei, Candida albicans, Candida cloaceae, Candida tropicalis, Candida utilis, Geotrichum candidum, Hansenula americana, Hansenula anomala, Hansenula wingei,* and *Aspergillus oryzae.*

The formulated yeast may also include bacteria cell wall derived agents such as peptidoglycan and other components derived from gram-positive bacteria with a high content of peptidoglycan. Exemplary gram-positive bacteria include *Lactobacillus acidophilus, Bifedobact thermophilum, Bifedobat longhum, Streptococcus faecium, Bacillus pumilus, Bacillus subtilis, Bacillus licheniformis, Lactobacillus acidophilus, Lactobacillus casei, Enterococcus faecium, Bifidobacterium bifidium, Propionibacterium acidipropionici, Propionibacteriium freudenreichii,* and *Bifidobacterium pseudolongum.*

The amount of formulated yeast can and will vary depending on the formulated yeast, the type of non-human animal that will be administered the feed composition, the body weight, sex, and medical condition of the non-human animal among other variables, and can be determined experimentally. The concentration of formulated yeast in the feed composition may range from about 0.01 lb/ton of feed to about 1 lb/ton of feed, from about 0.1 lb/ton of feed to about 2 lb/ton of feed, from about 0.5 lb/ton of feed to about 1 lb/ton of feed, or from about 0.1 lb/ton of feed to about 1 lb/ton of feed. Preferably, the concentration of *Capsicum* product in the feed composition ranges from about 0.3 lb/ton of feed to about 0.7 lb/ton of feed.

(c) *Capsicum* Product

The term "*Capsicum* product" as used herein refers to any product derived from the fruit of a plant in the *Capsicum* genus. *Capsicum* is a genus of plants from the nightshade family (Solanaceae). The fruit of *Capsicum* plant have a variety of names. They are commonly called chili pepper, hot pepper, red or green pepper. Herein, they are referred to as peppers. Some of these plants are used as spices, vegetables, or drugs.

The fruit of *Capsicum* plants generally comprise capsaicinoids. Capsaicinoids are the name given to the class of compounds found present in members of the *Capsicum* family of plants. Capsaicinoids are vanilloids, the heaviest of this class of compound in nature. Other vanilloids include vanillin, present in vanilla and the wood used to age wine, eugenol, present in bay leaves, allspice, and cloves, and zingerone, giving ginger and mustard their distinct flavors. The most common capsaicinoid is N-Vanillyl-8-methyl-6-(E)-noneamide (capsaicin). Nearly as common is Dihydrocapsaicin. Other capsaicinoids are nordihydrocapsaicin, homocapsaicin, and homodihydrocapsaicin. These and other capsaicinoids occur in varying ratios from plant to plant.

A *Capsicum* product may be any product comprising one or more of capsaicin, dihydrocapsaicin, capsaicinoids, *Capsicum* oleoresin, vanilloids, macerated hot peppers, ground hot peppers, extract from hot peppers, other capsaicin- or *Capsicum*-containing plant materials, an encapsulated or coated *Capsicum* product, and combinations of any thereof.

A *Capsicum* product may comprise one or more capsaicinoid. A capsaicinoid may be synthetic capsaicinoids, a capsaicinoid extract from the fruits of members of the *Capsicum* family, or combinations thereof. Preferably, a capsaicinoid is a *Capsicum* oleoresin. *Capsicum* oleoresin is a concentrate of capsaicinoids that generally contains about 0.1% to 50% by weight of natural or synthetic capsaicinoids. Capsaicinoids, especially when concentrated in the form of *Capsicum* oleoresin, are toxic, requiring strict handling conditions not available for use by animal feed manufacturers. As such, a capsaicinoid may be formulated for safe handling. Methods of formulating capsaicinoids for safe handling are known in the art. For instance, capsaicinoids may be in the form of capsules, microencapsulated formulations, caplets, and granules.

Preferably, a *Capsicum* product comprises ground peppers. Ground peppers may be the ground fruit of any *Capsicum* plant. Preferably, ground peppers are the ground fruit of a hot pepper. Ground peppers may further be formulated for safe and easy handling by animal feed manufacturers. For instance, ground pepper may be pelleted or encapsulated. A preferred *Capsicum* product is encapsulated ground pepper. More preferably, a *Capsicum* product is encapsulated ground pepper comprising about 30% to about 70% ground peppers, preferably about 40% to about 60% ground peppers, and more preferably about 45% to about 55% ground peppers. Encapsulated ground peppers and methods of encapsulating ground peppers are known in the art.

Generally, the amount of *Capsicum* product in a feed additive composition can and will vary depending on the *Capsicum* product, the type of non-human animal that will be administered the feed additive composition, the body weight, sex, and medical condition of the non-human animal that will be administered the feed additive composition.

Generally, a *Capsicum* product comprises about 0.05% to about 1% capsaicinoids, preferably about 0.1% to about 0.7% capsaicinoids, and more preferably about 0.4% to about 0.6% capsaicinoids. Irrespective of the capsaicinoid concentration in a *Capsicum* product, a feed additive composition comprises an amount of *Capsicum* product to provide from about 0.05% to about 5%, preferably from about 0.1% to about 2% capsaicinoids in the feed additive composition.

The amount of *Capsicum* product in a feed composition can and will vary depending on the *Capsicum* product, the type of non-human animal that will be administered the feed composition, the body weight, sex, and medical condition of the non-human animal among other variables, and can be determined experimentally. The concentration of *Capsicum* product in the feed composition may range from about 0.01 lb/ton of feed to about 1 lb/ton of feed, from about 0.1 lb/ton of feed to about 2 lb/ton of feed, from about 0.5 lb/ton of feed to about 1 lb/ton of feed, or from from about 0.1 lb/ton of feed to about 1 lb/ton of feed. Preferably, the concentration of *Capsicum* product in the feed composition ranges from about 0.1 lb/ton of feed to about 0.5 lb/ton of feed.

(d) Antimicrobial Clay

As used herein, the term "antimicrobial clay" may be any clay having antimicrobial properties. An antimicrobial clay may be capable of controlling any one or more of bacteria, viruses, protozoans such as *Cryptosporidium* spp. and *giardia,* and fungi such as mold and mildew. As used herein, the term "antimicrobial" is used to indicate that antimicrobial clay may either kill microbes, and therefore be "microbicidal," or prevents microbes from growing and reproducing while not necessarily killing them otherwise, and therefore be "biostatic." Methods of determining if an agent, including clay, has antimicrobial properties are known in the art, and generally comprise contacting microbes with the agent in vivo or in vitro, and determining the effect of the agent on growth of the microbe.

Antimicrobial clays suitable for an animal feed composition are known in the art, and may be as disclosed in U.S. Application No. 15/266,570. Preferably, an antimicrobial clay suitable for a feed composition of the disclosure comprises a naturally mined antimicrobial clay. Non-limiting examples of naturally-mined antimicrobial clays include clays supplied by Oregon Mineral Technologies (OMT; Grants Pass, Oregon), also known as blue clay. The source of the blue clay is an open pit mine in hydrothermally altered, pyroclastic material in the Cascade Mountains. Also preferred is a natural red clay mined in the Cascade Mountain region of Oregon, more specifically a red clay mined in the crater lake region of the Cascade Mountains of Oregon.

The amount of antimicrobial clay in a feed composition can and will vary depending on the antimicrobial clay, the type of non-human animal that will be administered the feed composition, the body weight, sex, and medical condition of the non-human animal among other variables, and can be determined experimentally. The concentration of antimicrobial clay in the feed composition may range from about 0.1 lb/ton of feed to about 100 lb/ton of feed, from about 0.1 lb/ton of feed to about 10 lb/ton of feed, from about 1 lb/ton of feed to about 50 lb/ton of feed, or from from about 1 lb/ton of feed to about 10 lb/ton of feed. Preferably, the concentration of antimicrobial clay in the feed composition ranges from about 2 lb/ton of feed to about 6 lb/ton of feed.

(e) Basal Animal Diet

A basal animal diet suitable for a feed composition of the disclosure can and will vary depending on the intended animal, the weight of the animal, and the stage of development of the animal among other variables.

The terms “feed”, “food”, and “feed formulation” are used herein interchangeably and may refer to any feed composition normally fed to an animal. Basal animal diets normally fed to an animal are known in the art. A basal animal diet may include one or more components of an animal feed. Non-limiting examples of feed matter or animal feed matter may include, without limitation: corn or a component of corn, such as, for example, corn meal, corn fiber, corn hulls, corn DDGS (distiller’s dried grain with solubles), silage, ground corn, corn germ, corn gluten, corn oil, or any other portion of a corn plant; soy or a component of soy, such as, for example, soy oil, soy meal, soy hulls, soy silage, ground soy, or any other portion of a soy plant; wheat or any component of wheat, such as, for example, wheat meal, wheat fiber, wheat hulls, wheat chaff, ground wheat, wheat germ, or any other portion of a wheat plant; rice or any component of rice, such as, for example, rice meal, rice fiber, rice hulls, rice chaff, ground rice, rice germ, or any other portion of a rice plant; canola, such as, for example, canola oil, canola meal, canola protein, canola hulls, ground canola, or any other portion of a canola plant; sunflower or a component of a sunflower plant; sorghum or a component of a sorghum plant; sugar beet or a component of a sugar beet plant; cane sugar or a component of a sugarcane plant; barley or a component of a barley plant; palm oil, palm kernel or a component of a palm plant; glycerol; corn steep liquor; a waste stream from an agricultural processing facility; lecithin; rumen protected fats; molasses; soy molasses; flax; peanuts; peas; oats; grasses, such as orchard grass and fescue; fish meal, meat & bone meal; feather meal; and poultry byproduct meal; and alfalfa and/or clover used for silage or hay, and various combinations of any of the feed ingredients set forth herein, or other feed ingredients generally known in the art. As it will be recognized in the art, a basal animal diet may further be supplemented with amino acids, vitamins, minerals, and other feed additives such as other types of enzymes, organic acids, essential oils, probiotics, prebiotics, antioxidants, pigments, anti-caking agents, and the like, as described further below. A basal animal diet may be formulated for administration to any animal subject. Animal subjects may be as described below.

The basal animal diets may optionally comprise at least one additional nutritive and/or pharmaceutical agent. For instance, the at least one additional nutritive and/or pharmaceutical agent may be selected from the group consisting of vitamin, mineral, amino acid, antioxidant, probiotic, essential fatty acid, and pharmaceutically acceptable excipient. The compositions may include one additional nutritive and/or pharmaceutical component or a combination of any of the foregoing additional components in varying amounts. Suitable examples of each additional component are detailed below.

(i) Vitamins

Optionally, the animal feed formulation may include one or more vitamins. Suitable vitamins for use in the dietary supplement include vitamin C, vitamin A, vitamin E, vitamin B12, vitamin K, riboflavin, niacin, vitamin D, vitamin B6, folic acid, pyridoxine, thiamine, pantothenic acid, and biotin. The form of the vitamin may include salts of the vitamin, derivatives of the vitamin, compounds having the same or similar activity of a vitamin, and metabolites of a vitamin.

The animal feed formulation may include one or more forms of an effective amount of any of the vitamins described herein or otherwise known in the art. Exemplary vitamins include vitamin K, vitamin D, vitamin C, and biotin. An “effective amount” of a vitamin typically quantifies an amount at least about 10% of the United States Recommended Daily Allowance (“RDA”) of that particular vitamin for a subject. It is contemplated, however, that amounts of certain vitamins exceeding the RDA may be beneficial for certain animals. For example, the amount of a given vitamin may exceed the applicable RDA by 100%, 200%, 300%, 400%, 500% or more.

(ii) Minerals

Generally, the animal feed formulation may include one or more minerals or mineral sources. Non-limiting examples of minerals include, without limitation, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

Generally speaking, the animal feed formulation may include one or more forms of an effective amount of any of the minerals described herein or otherwise known in the art. An “effective amount” of a mineral typically quantifies an amount at least about 10% of the United States Recommended Daily Allowance (“RDA”) of that particular mineral for a subject. It is contemplated, however, that amounts of certain minerals exceeding the RDA may be beneficial for certain subjects. For example, the amount of a given mineral may exceed the applicable RDA by 100%, 200%, 300%, 400%, 500% or more. Typically, the amount of mineral included in the dietary supplement may range from about 1 mg to about 1500 mg, about 5 mg to about 500 mg, or from about 50 mg to about 500 mg per dosage.

(iii) Essential Fatty Acids

Optionally, the animal feed formulation may include a source of an essential fatty acid. The essential fatty acid may be isolated or it may be an oil source or fat source that contains an essential fatty acid. In one embodiment, the essential fatty acid may be a polyunsaturated fatty acid (PUFA), which has at least two carbon-carbon double bonds generally in the cis-configuration. The PUFA may be a long chain fatty acid having at least 18 carbons atoms. The PUFA may be an omega-3 fatty acid in which the first double bond occurs in the third carbon-carbon bond from the methyl end of the carbon chain (i.e., opposite the carboxyl acid group). Examples of omega-3 fatty acids include alpha-linolenic acid (18:3, ALA), stearidonic acid (18:4), eicosatetraenoic acid (20:4), eicosapentaenoic acid (20:5; EPA), docosatetraenoic acid (22:4), n-3 docosapentaenoic acid (22:5; n-3DPA), and docosahexaenoic acid (22:6; DHA). The PUFA may also be an omega-5 fatty acid, in which the first double bond occurs in the fifth carbon-carbon bond from the methyl end. Exemplary omega-5 fatty acids include myristoleic acid (14:1), myristoleic acid esters, and cetyl myristoleate. The PUFA may also be an omega-6 fatty acid, in which the first double bond occurs in the sixth carbon-carbon bond from the methyl end. Examples of omega-6 fatty acids include linoleic acid (18:2), gamma-linolenic acid (18:3), eicosadienoic acid (20:2), dihomo-gamma-linolenic acid (20:3), arachidonic acid (20:4), docosadienoic acid (22:2), adrenic acid (22:4), and n-6 docosapentaenoic acid (22:5). The fatty acid may also be an omega-9 fatty acid, such as oleic acid (18:1), eicosenoic acid (20:1), mead acid (20:3), erucic acid (22:1), and nervonic acid (24:1).

In another embodiment, the essential fatty acid source may be a seafood-derived oil. The seafood may be a vertebrate fish or a marine organism, such that the oil may be fish oil or marine oil. The long chain (20C, 22C) omega-3 and omega-6 fatty acids are found in seafood. The ratio of omega-3 to omega-6 fatty acids in seafood ranges from about 8:1 to 20:1. Seafood from which oil rich in omega-3 fatty acids may be derived include, but are not limited to, abalone scallops, albacore tuna, anchovies, catfish, clams, cod, gem fish, herring, lake trout, mackerel, menhaden, orange roughy, salmon, sardines, sea mullet, sea perch, shark, shrimp, squid, trout, and tuna.

In yet another embodiment, the essential fatty acid source may be a plant-derived oil. Plant and vegetable oils are rich in omega-6 fatty acids. Some plant-derived oils, such as flaxseed oil, are especially rich in omega-3 fatty acids. Plant or vegetable oils are generally extracted from the seeds of a plant, but may also be extracted from other parts of the plant. Plant or vegetable oils that are commonly used for cooking or flavoring include, but are not limited to, acai oil, almond oil, amaranth oil, apricot seed oil, argan oil, avocado seed oil, babassu oil, ben oil, blackcurrant seed oil, Borneo tallow nut oil, borage seed oil, buffalo gourd oil, canola oil, carob pod oil, cashew oil, castor oil, coconut oil, coriander seed oil, corn oil, cottonseed oil, evening primrose oil, false flax oil, flax seed oil, grapeseed oil, hazelnut oil, hemp seed oil, kapok seed oil, lallemantia oil, linseed oil, macadamia oil, meadowfoam seed oil, mustard seed oil, okra seed oil, olive oil, palm oil, palm kernel oil, peanut oil, pecan oil, pequi oil, perilla seed oil, pine nut oil, pistachio oil, poppy seed oil, prune kernel oil, pumpkin seed oil, quinoa oil, ramtil oil, rice bran oil, safflower oil, sesame oil, soybean oil, sunflower oil, tea oil, thistle oil, walnut oil, or wheat germ oil. The plant-derived oil may also be hydrogenated or partially hydrogenated.

In still a further embodiment, the essential fatty acid source may be an algae-derived oil. Commercially available algae-derived oils include those from *Crypthecodinium cohnii* and *Schizochytrium* sp. Other suitable species of algae, from which oil is extracted, include *Aphanizomenon flos-aquae, Bacilliarophy* sp., *Botryococcus braunii, Chlorophyceae* sp., *Dunaliella tertiolecta, Euglena gracilis, Isochrysis galbana, Nannochloropsis salina, Nannochloris* sp., *Neochloris oleoabundans, Phaeodactylum tricornutum, Pleurochrysis carterae, Prymnesium parvum, Scenedesmus dimorphus, Spirulina* sp., and *Tetraselmis chui.*

(iv) Amino Acids

The animal feed formulation may optionally include from one to several amino acids. Suitable amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine or their hydroxy analogs. In certain embodiments, the amino acid will be selected from the essential amino acids. An essential amino acid is generally described as one that cannot be synthesized de novo by the organism, and therefore, must be provided in the diet. By way of non-limiting example, the essential amino acids for humans include: L-histidine, L-isoleucine, L-leucine, L-lysine, L-methionine, L-phenylalanine, L-valine and L-threonine.

(v) Antioxidants

The animal feed formulation may include one or more suitable antioxidants. As will be appreciated by a skilled artisan, the suitability of a given antioxidant will vary depending upon the species to which the dietary supplement will be administered. Non-limiting examples of antioxidants include ascorbic acid and its salts, ascorbyl palmitate, ascorbyl stearate, anoxomer, N-acetylcysteine, benzyl isothiocyanate, o-, m- or p-amino benzoic acid (o is anthranilic acid, p is PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, p-coumaric acid, curcurin, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), eugenol, ferulic acid, flavonoids, flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytryrosol, hydroxyurea, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, propyl gallate, polyphosphates, quercetin, trans-resveratrol, rosmarinic acid, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., Ionox 100), 2,4-(tris-3',5'-bitert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, zeaxanthin, or combinations thereof.

Natural antioxidants that may be included in the dietary supplement include, but are not limited to, apple peel extract, blueberry extract, carrot juice powder, clove extract, coffee berry, coffee bean extract, cranberry extract, eucalyptus extract, ginger powder, grape seed extract, green tea, olive leaf, parsley extract, peppermint, pimento extract, pomace, pomegranate extract, rice bran extract, rosehips, rosemary extract, sage extract, tart cherry extract, tomato extract, turmeric, and wheat germ oil.

(vi) Anti-Inflammatory Agents

The animal feed formulation may optionally include at least one anti-inflammatory agent. In one embodiment, the anti-inflammatory agent may be a synthetic non-steroidal anti-inflammatory drug (NSAID) such as acetylsalicylic acid, dichlophenac, indomethacin, oxamethacin, ibuprofen, indoprofen, naproxen, ketoprofen, mefamanic acid, metamizole, piroxicam, and celecoxib. In an alternate embodiment, the anti-inflammatory agent may be a prohormone that modulates inflammatory processes. Suitable prohormones having this property include prohormone convertase 1, proopiomelanocortin, prohormone B-type natriuretic peptide, SMR1 prohormone, and the like. In another embodiment, the anti-inflammatory agent may be an enzyme having anti-inflammatory effects. Examples of anti-inflammatory enzymes include bromelain, papain, serrapeptidase, and proteolytic enzymes such as pancreatin (a mixture of trypsin, amylase and lipase).

In still another embodiment, the anti-inflammatory agent may be a peptide with anti-inflammatory effects. For example, the peptide may be an inhibitor of phospholipase A2, such as antiflammin-1, a peptide that corresponds to amino acid residues 246-254 of lipocortin; antiflammin-2, a peptide that corresponds to amino acid residues 39-47 of uteroglobin; S7 peptide, which inhibits the interaction between interleukin 6 and interleukin 6 receptor; RP1, a prenyl protein inhibitor; and similar peptides. Alternatively, the anti-inflammatory peptide may be cortistatin, a cyclic neuropeptide related to somatostatin, or peptides that correspond to an N-terminal fragment of SV-IV protein, a conserved region of E-, L-, and P-selectins, and the like. Other suitable anti-inflammatory preparations include collagen hydrolysates and milk micronutrient concentrates (e.g., MicroLactin® available from Stolle Milk Biologics, Inc., Cincinnati, OH), as well as milk protein hydrolysates, casein hydrolysates, whey protein hydrolysates, and plant protein hydrolysates.

In a further embodiment, the anti-inflammatory agent may be a probiotic that has been shown to modulate inflammation. Suitable immunomodulatory probiotics include lactic acid bacteria such as acidophilli, lactobacilli, and bifidophilli. In yet another embodiment, the anti-inflammatory agent may be a plant extract having anti-inflammatory properties. Non-limiting examples of suitable plant extracts with anti-inflammatory benefits include blueberries, boswella, black catechu and Chinese skullcap, celery seed, chamomile, cherries, devils claw, eucalyptus, evening primrose, ginger, hawthorne berries, horsetail, Kalopanax pictus bark, licorice root, turmeric, white wallow, willow bark, and yucca.

(vii) Herbals

The animal feed formulation may optionally include at least one herb or herbal derivative. Suitable herbals and herbal derivatives, as used herein, refer to herbal extracts, and substances derived from plants and plant parts, such as leaves, flowers, and roots, without limitation. Non-limiting exemplary herbals and herbal derivatives include agrimony, alfalfa, aloe vera, amaranth, angelica, anise, barberry, basil, bayberry, bee pollen, birch, bistort, blackberry, black cohosh, black walnut, blessed thistle, blue cohosh, blue vervain, boneset, borage, buchu, buckthorn, bugleweed, burdock, *Capsicum,* cayenne, caraway, cascara sagrada, catnip, celery, centaury, chamomile, chaparral, chickweed, chicory, chinchona, cloves, coltsfoot, comfrey, cornsilk, couch grass, cramp bark, culver's root, cyani, cornflower, damiana, dandelion, devils claw, dong quai, echinacea, elecampane, ephedra, eucalyptus, evening primrose, eyebright, false unicorn, fennel, fenugreek, figwort, flaxseed, garlic, gentian, ginger, ginseng, golden seal, gotu kola, gum weed, hawthorn, hops, horehound, horseradish, horsetail, hoshouwu, hydrangea, hyssop, iceland moss, irish moss, jojoba, juniper, kelp, lady's slipper, lemon grass, licorice, lobelia, mandrake, marigold, marjoram, marshmallow, mistletoe, mullein, mustard, myrrh, nettle, oatstraw, oregon grape, papaya, parsley, passion flower, peach, pennyroyal, peppermint, periwinkle, plantain, pleurisy root, pokeweed, prickly ash, psyllium, quassia, queen of the meadow, red clover, red raspberry, redmond clay, rhubarb, rose hips, rosemary, rue, safflower, saffron, sage, St. John's wort, sarsaparilla, sassafras, saw palmetto, skullcap, senega, senna, shepherd's purse, slippery elm, spearmint, spikenard, squawvine, stillingia, strawberry, taheebo, thyme, uva ursi, valerian, violet, watercress, white oak bark, white pine bark, wild cherry, wild lettuce, wild yam, willow, wintergreen, witch hazel, wood betony, wormwood, yarrow, yellow dock, yerba santa, yucca and combinations thereof.

(viii) Pigments

The animal feed formulation may optionally include at least one pigment. Suitable non-limiting pigments include actinioerythrin, alizarin, alloxanthin, β-apo-2'-carotenal, apo-2-lycopenal, apo-6'-lycopenal, astacein, astaxanthin, azafrinaldehyde, aacterioruberin, aixin, α-carotine, β-carotine, γ-carotine, β-carotenone, canthaxanthin, capsanthin, capsorubin, citranaxanthin, citroxanthin, crocetin, crocetinsemialdehyde, crocin, crustaxanthin, cryptocapsin, α-cryptoxanthin, β-cryptoxanthin, cryptomonaxanthin, cynthiaxanthin, decaprenoxanthin, dehydroadonirubin, diadinoxanthin, 1,4-diamino-2,3-dihydroanthraquinone, 1,4-dihydroxyanthraquinone, 2,2'-diketospirilloxanthin, eschscholtzxanthin, eschscholtzxanthone, flexixanthin, foliachrome, fucoxanthin, gazaniaxanthin, hexahydrolycopene, hopkinsiaxanthin, hydroxyspheriodenone, isofucoxanthin, loroxanthin, lutein, luteoxanthin, lycopene, lycopersene, lycoxanthin, morindone, mutatoxanthin, neochrome, neoxanthin, nonaprenoxanthin, OH-Chlorobactene, okenone, oscillaxanthin, paracentrone, pectenolone, pectenoxanthin, peridinin, phleixanthophyll, phoeniconone, phoenicopterone, phoenicoxanthin, physalien, phytofluene, pyrrhoxanthininol, quinones, rhodopin, rhodopinal, rhodopinol, rhodovibrin, rhodoxanthin, rubixanthone, saproxanthin, semi-α-carotenone, semi-β-carotenone, sintaxanthin, siphonaxanthin, siphonein, spheroidene, tangeraxanthin, torularhodin, torularhodin methyl ester, torularhodinaldehyde, torulene, 1,2,4-trihydroxyanthraquinone, triphasiaxanthin, trollichrome, vaucheriaxanthin, violaxanthin, wamingone, xanthin, zeaxanthin, α-zeacarotene, or combinations thereof.

(ix) Pharmaceutical Acceptable Agents

The animal feed formulation may optionally include at least one pharmaceutical acceptable agent. Suitable non-limiting pharmaceutically acceptable agents include an acid/alkaline-labile drug, a pH dependent drug, or a drug that is a weak acid or a weak base. Examples of acid-labile drugs include statins (e.g., pravastatin, fluvastatin and atorvastatin), antiobiotics (e.g., penicillin G, ampicillin, streptomycin, erythromycin, clarithromycin and azithromycin), nucleoside analogs (e.g., dideoxyinosine (ddI or didanosine), dideoxyadenosine (ddA), dideoxycytosine (ddC), salicylates (e.g., aspirin), digoxin, bupropion, pancreatin, midazolam, and methadone. Drugs that are only soluble at acid pH include nifedipine, emonapride, nicardipine, amosulalol, noscapine, propafenone, quinine, dipyridamole, josamycin, dilevalol, labetalol, enisoprost, and metronidazole. Drugs that are weak acids include phenobarbital, phenytoin, zidovudine (AZT), salicylates (e.g., aspirin), propionic acid compounds (e.g., ibuprofen), indole derivatives (e.g., indomethacin), fenamate compounds (e.g., meclofenamic acid), pyrrolealkanoic acid compounds (e.g., tolmetin), cephalosporins (e.g., cephalothin, cephalaxin, cefazolin, cephradine, cephapirin, cefamandole, and cefoxitin), 6-fluoroquinolones, and prostaglandins. Drugs that are weak bases include adrenergic agents (e.g., ephedrine, desoxyephedrine, phenylephrine, epinephrine, salbutamol, and terbutaline), cholinergic agents (e.g., physostigmine and neostigmine), antispasmodic agents (e.g., atropine, methantheline, and papaverine), curariform agents (e.g., chlorisondamine), tranquilizers and muscle relaxants (e.g., fluphenazine, thioridazine, trifluoperazine, chlorpromazine, and triflupromazine), antidepressants (e.g., amitriptyline and nortriptyline), antihistamines (e.g., diphenhydramine, chlorpheniramine, dimenhydrinate, tripelennamine, perphenazine, chlorprophenazine, and chlorprophenpyridamine), cardioactive agents (e.g., verapamil, diltiazem, gallapomil, cinnarizine, propranolol, metoprolol and nadolol), antimalarials (e.g., chloroquine), analgesics (e.g., propoxyphene and meperidine), antifungal agents (e.g., ketoconazole and itraconazole), antimicrobial agents (e.g., cefpodoxime, proxetil, and enoxacin), caffeine, theophylline, and morphine. In another embodiment, the drug may be a biphosphonate or another drug used to treat osteoporosis. Non-limiting examples of a biphosphonate include alendronate, ibandronate, risedronate, zoledronate, pamidronate, neridronate, olpadronate, etidronate, clodronate, and tiludronate. Other suitable drugs include estrogen, selective estrogen receptor modulators (SERMs), and parathyroid hormone (PTH) drugs. In yet another embodiment, the drug may be an antibacterial agent. Suitable antibiotics include am inoglycosides (e.g., amikacin, gentamicin, kanamycin, neomycin, netilmicin, streptomycin, and tobramycin), carbecephems (e.g., loracarbef), a carbapenem (e.g., certapenem, imipenem, and meropenem), cephalosporins (e.g., cefadroxil cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, and ceftriaxone), macrolides (e.g., azithromycin, clarithromycin, dirithromycin, erythromycin, and troleandomycin), monobactam, penicillins (e.g., amoxicillin, ampicillin, carbenicillin, cloxacillin, dicloxacillin, nafcillin, oxacillin, penicillin G, penicillin V, piperacillin, and ticarcillin), polypeptides (e.g., bacitracin, colistin, and polymyxin B), quinolones (e.g., ciprofloxacin, enoxacin, gatifloxacin, levofloxacin, lomefloxacin, moxifloxacin, norfloxacin, ofloxacin, and trovafloxacin), sulfonamides (e.g., mafenide, sulfacetamide, sulfamethizole, sulfasalazine, sulfisoxazole, and trimethoprim-sulfamethoxazole), and tetracyclines (e.g., demeclocycline, doxycycline, minocycline, and oxytetracycline). In an alternate embodiment, the drug may be an antiviral protease inhibitor (e.g., amprenavir, fosamprenavir, indinavir, lopinavir/ritonavir, ritonavir, saquinavir, and nelfinavir). In still another embodiment, the drug may be a cardiovascular drug. Examples of suitable cardiovascular agents include cardiotonic agents (e.g., digitalis (digoxin), ubidecarenone, and dopamine), vasodilating agents (e.g., nitroglycerin, captopril, dihydralazine, diltiazem, and isosorbide dinitrate), antihypertensive agents (e.g., alpha-methyldopa, chlortalidone, reserpine, syrosingopine, rescinnamine, prazosin, phentolamine, felodipine, propanolol, pindolol, labetalol, clonidine, captopril, enalapril, and lisonopril), beta blockers (e.g., levobunolol, pindolol, timolol maleate, bisoprolol, carvedilol, and butoxamine), alpha blockers (e.g., doxazosin, prazosin, phenoxybenzamine, phentolamine, tamsulosin, alfuzosin, and terazosin), calcium channel blockers (e.g., amlodipine, felodipine, nicardipine, nifedipine, nimodipine, nisoldipine, nitrendipine, lacidipine, lercanidipine, verapamil, gallopamil, and diltiazem), monensin, avilamycin, salinomycin, narasin, diclaserol, tylosin, bacitracin, bacitracin zinc, and anticlot agents (e.g., dipyrimadole).

(x) Excipients

A variety of commonly used excipients in animal feed formulation may be selected on the basis of compatibility with the active ingredients. Non-limiting examples of suitable excipients include an agent selected from the group consisting of non-effervescent disintegrants, a coloring agent, a flavor-modifying agent, an oral dispersing agent, a stabilizer, a preservative, a diluent, a compaction agent, a lubricant, a filler, a binder, taste masking agents, an effervescent disintegration agent, and combinations of any of these agents.

In one embodiment, the excipient is a binder. Suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof. The polypeptide may be any arrangement of amino acids ranging from about 100 to about 300,000 daltons.

In another embodiment, the excipient may be a filler. Suitable fillers include carbohydrates, inorganic compounds, and polyvinylpirrolydone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, and sorbitol.

The excipient may comprise a non-effervescent disintegrant. Suitable examples of non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth.

In another embodiment, the excipient may be an effervescent disintegrant. By way of non-limiting example, suitable effervescent disintegrants include sodium bicarbonate in combination with citric acid and sodium bicarbonate in combination with tartaric acid.

The excipient may comprise a preservative. Suitable examples of preservatives include antioxidants, such as a-tocopherol or ascorbate, and antimicrobials, such as parabens, chlorobutanol or phenol.

In another embodiment, the excipient may include a diluent. Diluents suitable for use include pharmaceutically acceptable saccharides such as sucrose, dextrose, lactose, microcrystalline cellulose, fructose, xylitol, and sorbitol; polyhydric alcohols; a starch; pre-manufactured direct compression diluents; and mixtures of any of the foregoing.

The excipient may include flavors. Flavors incorporated into the outer layer may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oil, such as lemon oil, orange oil, grape and grapefruit oil, fruit essences including apple, peach, pear, strawberry, raspberry, cherry, plum, pineapple, and apricot.

In another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; sugar alcohols such as sorbitol, mannitol, sylitol, and the like.

In another embodiment, the excipient may be a lubricant. Suitable non-limiting examples of lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

The excipient may be a dispersion enhancer. Suitable dispersants may include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

Depending upon the embodiment, it may be desirable to provide a coloring agent in the outer layer. Suitable color additives include food, drug and cosmetic colors (FD&C), drug and cosmetic colors (D&C), or external drug and cosmetic colors (Ext. D&C). These colors or dyes, along with their corresponding lakes, and certain natural and derived colorants, may be suitable for use in the present invention depending on the embodiment.

The excipient may include a taste-masking agent. Taste-masking materials include, e.g., cellulose hydroxypropyl ethers (HPC) such as Klucel®, Nisswo HPC and PrimaFlo HP22; low-substituted hydroxypropyl ethers (L-HPC); cellulose hydroxypropyl methyl ethers (HPMC) such as Seppifilm-LC, Pharmacoat®, Metolose SR, Opadry YS, PrimaFlo, MP3295A, Benecel MP824, and Benecel MP843; methylcellulose polymers such as Methocel® and Metolose®; Ethylcelluloses (EC) and mixtures thereof such as E461, Ethocel®, Aqualon®-EC, Surelease; Polyvinyl alcohol (PVA) such as Opadry AMB; hydroxyethylcelluloses such as Natrosol®; carboxymethylcelluloses and salts of carboxymethylcelluloses (CMC) such as Aualon®-CMC; polyvinyl alcohol and polyethylene glycol co-polymers such as Kollicoat IR®; monoglycerides (Myverol), triglycerides (KLX), polyethylene glycols, modified food starch, acrylic polymers and mixtures of acrylic polymers with cellulose ethers such as Eudragit® EPO, Eudragit® RD100, and Eudragit® E100; cellulose acetate phthalate; sepifilms such as mixtures of HPMC and stearic acid, cyclodextrins, and mixtures of these materials. In other embodiments, additional taste-masking materials contemplated are those described in U.S. Pat. Nos. 4,851,226; 5,075,114; and 5,876,759, each of which is hereby incorporated by reference in its entirety.

In various embodiments, the excipient may include a pH modifier. In certain embodiments, the pH modifier may include sodium carbonate or sodium bicarbonate.

The amount and types of ingredients (i.e., metal chelate, chondro protective agents, vitamin, mineral, amino acid, antioxidant, yeast culture, and essential fatty acid), and other excipients useful in animal feed formulation, are described throughout the specification and the examples.

(II) Feed Additive Composition

One aspect of the present disclosure encompasses feed additive compositions for non-human animals comprising at least two of a direct fed microbial (DFM), a formulated yeast, a *Capsicum* product, and an antimicrobial clay. Other optional additives may be further included. The feed additive composition may be added to basal animal diet for administration to the non-human animals. The feed additive composition may be formulated with basal animal diets to prepare the feed compositions described in Section I.

In some embodiments, formulated yeast in a basal animal diet comprises about 80-100% yeast extract, more preferably about 99% yeast extract. The amount of formulated yeast in a feed additive composition can and will vary depending on the formulated yeast, the type of non-human animal that will be administered the feed additive composition comprising the formulated yeast, the body weight, sex, and medical condition of the non-human animal that will be administered the feed additive composition. Generally, a feed additive composition comprises about 30% to about 70% formulated yeast, preferably about 40% to about 60% formulated yeast, and more preferably about 45% to about 55% formulated yeast.

When a *Capsicum* product comprises ground peppers, a feed additive composition comprises about 5% to about 25% ground peppers, preferably about 10% to about 20% ground peppers. Preferably, the ground peppers are from a *Capsicum* product comprising encapsulated ground pepper in an amount ranging about 30% to about 70% ground peppers, preferably about 40% to about 60% ground peppers, and more preferably about 45% to about 55% ground peppers.

In various embodiments, a feed additive composition may be introduced to a basal animal diet by way of various methods, depending on whether the feed additive composition is in a liquid or solid form. Non-limiting examples of introducing the feed additive composition to a basal animal diet may be formulating the feed additive composition into the basal animal diet, top-dressing the solid composition of a basal animal diet, spraying a liquid feed additive composition onto a basal animal diet, or combinations thereof. It will be recognized that, when the feed additive is introduced to a basal animal diet, the amount of the feed additive introduced to a basal animal diet is sufficient to provide the therapeutically effective amount of the combination of formulated yeast and *Capsicum* product in the diet of the animal.

In addition to DFM and at least one of a formulated yeast, a *Capsicum* product, and an antimicrobial clay, a feed additive composition may further comprise at least one additional ingredient such as vitamins, minerals, amino acids, antioxidants, probiotics, essential fatty acids, and pharmaceutically acceptable excipients. Such ingredients may be as described in Section I(e) above. In some embodiments, a feed additive composition further comprises calcium carbonate, rice hulls, mineral oil, and calcium stearate.

(III) Methods of Using

Another aspect of the disclosure encompasses methods of using a feed composition. The methods comprise administering the animal feed composition to non-human animals. Preferably, a feed composition is administered to non-human animals orally. A feed composition may be as described in Section (I).

The timing and duration of administration of a composition of the invention to an animal can and will vary. The feed composition may be administered throughout the period of feeding the animal. Alternatively, the feed composition may be administered at specific periods during the growth and development of the animal. For instance, the feed composition may be administered during periods of heightened susceptibility of the animal to infection, such as during infancy. A composition may also be administered after a microbial infection is detected and for the duration of the infection. A composition may also be administered at various intervals. For instance, a composition may be administered daily, weekly, monthly, or over a number of months. In some embodiments, a composition is administered weekly. In other embodiments, a composition is administered monthly. In preferred embodiments, a composition is administered daily. As it will be recognized in the art, the duration of treatment can and will vary depending on the growth and health of the animal.

(a) Non-Human Animals

Non-human animals, in broad term, may be defined as any animal which exhibits improved growth, improved health, improved intestinal health, and reduced microbial pathogen counts after administration of the feed additive composition. In various embodiments, the non-human animal may be a livestock mammal varying in age and health. Non-limiting example of suitable livestock mammals may be beef cattle, horses, dairy cattle, veal, pigs, goats, sheep, bison, llama, or alpaca. In other embodiments, the non-human animal may be an avian species varying in age and health. Non-limiting examples of suitable avian species or poultry may be chickens, including broilers, layers, and breeders, ducks, game hens, geese, pheasants, guinea fowl/hens, quail, turkeys, and ratites, such as emus and ostrich. In another embodiment, the non-human animal may be a companion animal varying in age and health. Non-limiting examples of companion animals may be a dog, a cat, a bird, a hamster, or a Guinee pig. In a preferred embodiment, the non-human animal is selected from a group comprising growing pigs, calves, foals, kids (goats), lambs, cria, chicks, poults, ducklings, puppies, kittens, or combinations thereof. Most preferred, the non-human animals are chickens varying in age and health.

(b) Improved Performance

In some embodiments, the methods comprise using the feed additive to improve performance of the animal. "Improved performance", as defined herein, refers to a positive change in size and/or maturation over a period of time in the non-human animal. In various embodiments, the non-human animals may exhibit improved growth, including for example an increase in body weight gain, feed intake, average daily weight gain (ADG), a decrease in the feed conversion rate (FCR), an increase in the average daily food intake (ADFI), an improved overall body weight, and the ratio of F/G wherein the ratio of F/G is defined as the ADFI/ADG.

The non-human animals may exhibit a decrease in the feed conversion ratio of about 2.79% or more as compared to a control group without supplementation of the feed additive composition. The non-human animals may exhibit a reduced mortality of at least 10% or more as compared to a control group without supplementation of the feed additive composition. The non-human animals may show an improved body weight gain as defined as the percent increase of at least 2.71% as compared to a control group without supplementation of the feed additive composition.

(c) Improved Health

Still another aspect of the disclosure encompasses methods for improving the health of non-human animals. "Improved health", as defined herein, refers to a reduction of incidences of diarrhea, reduction in the number of days of diarrhea, a decrease in mortality, improving intestinal health, reducing microbial pathogens in the intestinal tract of the animal, a decrease in cytokine panel measuring TNF-alpha, decrease in immunocrit levels, or combinations thereof in the non-human animals as compared to a control group.

(d) Reduced Impact of Microbial Pathogens

Still another aspect of the disclosure encompasses methods for reducing the impact of microbial pathogens in the non-human animals. Reducing the impact of microbial pathogens may comprise improving the intestinal health and the reduction of microbial pathogens in the non-human animals. Reducing the impact of microbial pathogens may also comprise improving the general health and performance of non-human animals exposed to the microbial pathogens.

The term "microbial pathogens", as defined herein, refers to a micro-organism that has the potential to cause disease. An infection is the invasion and multiplication of pathogenic microbes in a subject. Disease is when the infection causes damage to the subject's vital functions or systems.

"Improved intestinal health" and the "reduction of microbial pathogens" refer to a reduction in the number of pathogens and a reduction of inflammation caused by the microbial pathogens in the non-human animal as compared to a control group. Non-limiting examples of pathogenic bacteria that may be controlled using a feed additive composition of the present disclosure include *Clostridium perfringens, Eimeria maxima, Aeromonas hydrophila, Yersinia enterocolitica, Vibrio* spp., *Leptospira* spp., *Mycobacterium ulcerans, Listeria* spp., pathogenic strains of *E. coli, Pseudomonas* spp. such as *aeruginosa, Enterococcus* spp., *Salmonella* spp., *Campylobacter* spp., *Staphylococcus* spp. such as epidermidis, *S. aureus* (MRSA), *M. smegmatis, Streptococcus* sp., *Clostridia,* and *M. marinum.*

In a preferred alternative of the embodiments, reducing the impact of microbial pathogens comprises reducing the impact of *C. perfringens* in broilers. In an alternative of the embodiments, reducing the impact of microbial pathogens comprises controlling necrotic enteritis in the chicken. In another alternative, reducing the impact of microbial pathogens comprises controlling the impact of *C. perfringens* in combination with a coccidiosis challenge in disease-challenged broilers.

(e) Improved Quality

Another aspect of the disclosure encompasses methods for improving the quality of a product derived from a non-human animal. For instance, when the non-human animal is a chicken, an improved breast meat yield, reduced product variability, reduced impact on consumer appeal due to poor color, poor texture, and drip loss in retail display, reduced organoleptic qualities in cooked chicken including incidence of woody breast.

DEFINITIONS

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

Unless otherwise defined herein, scientific and technical terms used in connection with the present disclosure shall have the meanings that are commonly understood by those of ordinary skill in the art. The meaning and scope of the terms should be clear; however, in the event of any latent ambiguity, definitions provided herein take precedent over any dictionary or extrinsic definition. Further, unless otherwise required by context, singular terms as used herein and in the claims shall include pluralities, and plural terms shall include the singular.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges can independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

As used herein, the terms "about" and "approximately" designate that a value is within a statistically meaningful range. Such a range can be typically within 20%, more typically still within 10%, and even more typically within 5% of a given value or range. The allowable variation encompassed by the terms "about" and "approximately" depends on the particular system under study and can be readily appreciated by one of ordinary skill in the art.

As used herein, "administering" is used in its broadest sense to mean contacting a non-human animal with a composition disclosed herein.

The phrases "therapeutically effective amount" and "antimicrobial effective amount" are used interchangeably to mean an amount that is intended to qualify the amount of an agent or compound, that when administered, it will achieve the goal of healing an infection site, inhibiting the growth of a microorganism, or otherwise benefiting the recipient environment.

The terms "isolated", "purified", or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. "Purify" or "purification" in other embodiments means removing at least one contaminant from the composition to be purified. In this sense, purification does not require that the purified compound be homogenous, e.g., 100% pure.

As used herein, the terms "treating", "treatment", or "to treat" each may mean to alleviate, suppress, repress, eliminate, prevent or slow the appearance of symptoms, clinical signs, or underlying pathology of a condition or disorder on a temporary or permanent basis. Preventing a condition or disorder involves administering an agent of the present invention to a subject prior to onset of the condition. Suppressing a condition or disorder involves administering an agent of the present invention to a subject after induction of the condition or disorder but before its clinical appearance. Repressing the condition or disorder involves administering an agent of the present invention to a subject after clinical appearance of the disease. Prophylactic treatment may reduce the risk of developing the condition and/or lessen its severity if the condition later develops. For instance, treatment of a microbial infection may reduce, ameliorate, or altogether eliminate the infection, or prevent it from worsening.

Having described the invention in detail, it will be apparent that modifications and variations are possible without departing from the scope of the invention defined in the appended claims.

CITATIONS

1. Cobb-Vantress, Inc. 2012. Broiler management guide. Cobb-Vantress Inc., Siloam Springs, Ariz.

2. Hofacre, C. L., R. Froyman, B. George, M. A. Goodwin, and J. Brown. 1998. Use of Aviguard, virginiamycin or bacitracin MD against *Clostridium perfringens*-associated necrotizing enteritis. *J. Appl. Poult. Res.* 7:412-418.

EXAMPLES

The following examples illustrate various embodiments of the invention.

Example 1: Determine the Effect of Feeding Ground Peppers to Broilers Challenged with *E. maxima* and *C. perfringens*

This study was conducted to evaluate the effects of ground peppers in broilers challenged with *Eimeria maxima* and *Clostridium perfringens.* In this and all subsequent examples, ground peppers refers to encapsulated ground peppers comprising 50% ground peppers and 50% encapsulating material. A total of 256 day-old male Cobb×Cobb chicks were obtained from a commercial hatchery. Chicks were vaccinated for Marek's and reovirus at the hatchery. The birds were randomly assigned to 32 battery cages with eight chicks per cage. A total of five treatments (Table 1) were allotted, resulting in eight cages per treatment. Temperature and lighting were adjusted according to the husbandry guidelines of the Cobb broiler (Cobb, 2012). Each cage was equipped with a feed and water trough. Water and feed were provided ad libitum. The chicks were fed a 22.5% crude protein corn soybean-based diet (Table 2) through 28-d post-hatching. The diet was representative of a local commercial formulation and calculated analyses met or exceeded NRC broiler starter requirements. Experimental treatment feeds were prepared from this non-medicated basal starter feed.

TABLE 1

| Experimental treatments | | | | | |
|---|---|---|---|---|---|
| Treatment | Testing product | Conc. of Testing Product | *E. maxima* Challenge | *C. perfringens* Challenge | # of Cages |
| A | No Additive | None | DOT[1] 14 | None | 8 |
| B | No Additive | None | DOT 14 | DOT 19, 20, and 21 | 8 |
| C | BMD | 50.0 g/ton | DOT 14 | DOT 19, 20, and 21 | 8 |
| D | Encapsulated ground pepper | 300 g/ton | DOT 14 | DOT 19, 20, and 21 | 8 |

[1]Day of hatch

Encapsulated ground peppers comprise 50% ground peppers and 50% encapsulating material.

Capsaicinoid content of encapsulated ground pepper is 0.5%

TABLE 2

| Composition of the basal diet[1] | |
|---|---|
| | Kg/ton |
| Ingredients | |
| Corn, Yellow Grain | 556.29 |
| Soybean Meal Dehulled, Solvent | 377.55 |
| Fat, Vegetable | 25.55 |
| Dicalcium Phosphate | 20.39 |
| Calcium Carbonate | 10.31 |
| Salt, (NaCl) | 4.61 |
| Methionine, MHA | 3.08 |
| L - LYSINE, 98.5% | 0.82 |
| Trace Mineral Premix | 0.75 |
| Vitamin Premix | 0.65 |
| Total | 1000.00 |
| Calculated Nutrients Composition | |
| Crude Protein, % | 22.45 |
| Fat, % | 4.85 |
| Crude Fiber, % | 2.19 |
| ME, kcal/Kg | 3054.00 |
| Lysine, % | 1.34 |
| Methionine, % | 0.63 |
| Threonine, % | 0.92 |
| Calcium, % | 0.92 |
| Phosphorus, % | 0.45 |
| Phosphorus, Available, % | 0.67 |
| Ca/P Ratio | 2.04 |
| Sodium, % | 0.21 |

[1]Basal diet was prepared by Southern Poultry Research

Bird Allocation and Cage Randomization

Cages were blocked by location in the battery. The study began when the birds were placed (day of hatch) (DOT 0) at which time they were allocated to the experimental cages. No birds were replaced during the course of the study.

Cage Weights

All birds were weighed on DOT 0, 14, 21, and 28. Feed was weighed on DOT 0 and remaining feed was weighed on DOT 14, 21, and 28.

Disease Induction

On DOT 14, all birds were orally inoculated with ~5,000 oocysts of *E. maxima.* Starting on DOT 19, all birds, except Treatment 1 (Control) were given a broth culture of *C. perfringens* ~$10^8$ cfu/ml. The birds were administered a fresh broth culture once daily for 3 days (on DOTs 19, 20, and 21).

Necrotic Enteritis Intestinal Lesion Scoring

On DOT 21, three birds from each cage were selected, sacrificed, weighed, and examined for the degree of presence of Necrotic Enteritis lesions. If less than three birds were present at time of scoring, all remaining birds within the cage were scored. The scoring was based on a 0 to 3 score, with 0 being normal and 3 being the most severe. (Hofacre et al., 1998).

Management

The facility was checked at least twice daily to assure that all cages had water and that feed was available in every cage. The birds were watched closely for any abnormal conditions. The building temperature's range was maintained at an appropriate temperature for the age of the birds. Even, continuous light was provided by fluorescent lamps hung vertically along the wall. Feed and water was given ad libitum. When dead birds were removed from cages, the cage number, date, weight of the bird, sex, and probable cause of death were recorded.

Data was analyzed using one-way ANOVA by the MIXED procedure of SAS for this complete randomized design. Cage served as the experimental unit. The statistical model included cage weight gain, feed consumption, feed conversion, necrotic enteritis lesion scores, and % necrotic enteritis related mortality were calculated. All results were reported as least squares means. The significance level chosen was $\alpha=0.05$. Treatment effect was considered significant if $P<0.05$, whereas values between $0.05 \leq P \leq 0.10$ were considered as statistical trends.

Results

Broilers fed ground peppers had increased ($P<0.05$) body weight gain during the challenge and post challenge periods (d 14-28) compared to the challenge control birds (Table 3). Birds fed ground peppers had similar body weight gains as the unchallenged controls during this period of age. During all periods, body weight gain was numerically increased in birds fed ground peppers compared to the challenge controls. No significant differences were observed in feed conversion ratio (FCR) compared to the challenged control and birds fed ground peppers. Necrotic enteritis lesion scores and necrotic enteritis related mortality were lower ($P<0.05$) in birds fed the ground peppers compared to the challenged control birds. No differences were observed between the BMD (bacitracin methylene disalycilate) fed birds and the birds fed ground peppers in lesion scores or percent necrotic enteritis related mortality, suggesting that the ground peppers was effective in controlling *C. perfringens* disease challenge. No differences were noted in feed intake between all treatments.

TABLE 3

Summary 2017 SPRG NQ NE0117 ground peppers Trial

| Variable | Treatment: Non Challenged Control | Treatment: Challenged Control | Treatment: Challenged BMD | Treatment: Challenged Ground peppers | PSE | P-value |
|---|---|---|---|---|---|---|
| No. of Cages | 8 | 8 | 8 | 8 | | |
| No. of Birds | 64 | 64 | 64 | 64 | | |
| *C. Perfringens* Challenge | − | + | + | + | | |
| Live performance, 0-21 d | | | | | | |
| Feed consumption, Kg | 0.77 | 0.81 | 0.79 | 0.81 | 0.03 | 0.53 |
| Body weight gain, Kg | 0.46 | 0.43 | 0.44 | 0.43 | 0.02 | 0.33 |
| Feed Conversion | $1.66^a$ | $1.92^b$ | $1.79^{ab}$ | $1.89^b$ | 0.04 | 0.001 |
| Live performance, 14-21 d | | | | | | |
| Feed consumption, Kg | 0.39 | 0.42 | 0.41 | 0.42 | 0.02 | 0.63 |
| Body weight gain, Kg | $0.21^a$ | $0.14^b$ | $0.16^b$ | $0.16^b$ | 0.01 | 0.0001 |
| Feed Conversion | $1.90^a$ | $2.99^c$ | $2.56^b$ | $2.67^{bc}$ | 0.12 | <.0001 |
| Live performance, 14-28 d | | | | | | |
| Feed consumption, Kg | 0.88 | 0.92 | 0.95 | 1.07 | 0.10 | 0.53 |
| Body weight gain, Kg | $0.46^a$ | $0.32^b$ | $0.37^{ab}$ | $0.44^a$ | 0.03 | 0.02 |
| Feed Conversion | $1.92^a$ | $2.97^b$ | $2.58^b$ | $2.49^b$ | 0.15 | 0.0004 |
| Live performance, 0-28 d | | | | | | |
| Feed consumption, Kg | 1.23 | 1.18 | 1.22 | 1.35 | 0.07 | 0.38 |
| Body weight gain, Kg | 0.71 | 0.60 | 0.65 | 0.71 | 0.04 | 0.15 |
| Feed Conversion | $1.73^a$ | $1.96^b$ | $1.88^b$ | $1.92^b$ | 0.04 | 0.003 |
| Necrotic enteritis lesion score | $0.0^a$ | $1.5^c$ | $1.1^b$ | $1.1^b$ | 0.1 | <.0001 |
| Necrotic enteritis related mortality, % | $0.0^a$ | $48.4^c$ | $28.1^b$ | $26.6^b$ | 4.0 | <.0001 |

$^{a,b,c}$Means without a common superscript differ ($P < 0.05$)

Example 2: Determine the Effect of Feeding Ground Peppers to Broilers Challenged with *C. perfringens*

This study was conducted to evaluate the effects of ground peppers at two inclusion levels in broilers raised in pens on new litter and pens top dressed with litter comprising *C. perfringens* from a previous necrotic enteritis (NE) challenge study (Table 4). A total of 1200 day-old male Ross×Ross chicks were obtained from a commercial hatchery. Chicks were vaccinated for Marek's and reovirus at the hatchery.

TABLE 4

Experimental treatments

| Treatment | Test product | Litter Type | Starter DOT[1] 0-13 | Grower DOT 14-35 | Finisher DOT 14-35 | # of Pens |
|---|---|---|---|---|---|---|
| A | Encapsulated ground pepper | New | 0.15 Kg/ton | 0.15 Kg/ton | 0.15 Kg/ton | 8 |
| B | Encapsulated ground pepper | New | 0.3 Kg/ton | 0.3 Kg/ton | 0.3 Kg/ton | 8 |
| C | No Additive | New | None | None | None | 8 |
| D | Encapsulated ground pepper | Reused | 0.15 Kg/ton | 0.15 Kg/ton | 0.15 Kg/ton | 8 |
| E | Encapsulated ground pepper | Reused | 0.3 Kg/ton | 0.3 Kg/ton | 0.3 Kg/ton | 8 |
| F | No Additive | Reused | None | None | None | 8 |

[1]Day of hatch

Capsaicinoid content of encapsulated ground pepper is 0.5%

Experimental Diets

Feed consisted of non-medicated commercial-type broiler starter, grower, and finisher diets compounded according to meet or exceed NRC nutrient guidelines and contained feedstuffs commonly used in the United States (Table 5). Rations were fed ad libitum from date of chick arrival as follows: Starter—DOT 0 until DOT 15, grower DOT 15 to DOT 35, and finisher from DOT 35 to DOT 42 (study termination). Diets were fed as crumbles (starter feed) or pellets (grower and finisher feed). Pelleting of diets (grower and finisher diets) were manufactured with a California Pellet mill (at 80° C.). Experimental treatment feeds were prepared from a basal feed formulation.

TABLE 5

| Composition of the basal diet | | | |
|---|---|---|---|
| | Starter | Grower | Finisher |
| Ingredients, kg/ton | | | |
| Corn, Yellow Grain | 556.29 | 615.34 | 640.07 |
| Soybean Meal Dehulled, Solvent | 377.55 | 318.36 | 293.02 |
| Fat, Vegetable | 25.55 | 29.11 | 31.1 |
| Dicalcium Phosphate | 20.39 | 18.94 | 17.86 |
| Calcium Carbonate | 10.31 | 9.85 | 9.18 |
| Salt, (NaCl) | 4.61 | 4.39 | 4.41 |
| Methionine, MHA | 3.08 | 2.06 | 2.22 |
| L - LYSINE, 98.5% | 0.82 | 0.70 | 0.89 |
| Trace Mineral Premix | 0.75 | 0.70 | 0.75 |
| Vitamin Premix | 0.65 | 0.50 | 0.5 |
| Total | 1000.00 | 1000.00 | 1000.00 |
| Calculated Nutrients Composition | | | |
| Crude Protein, % | 22.45 | 20.0 | 19.0 |
| Fat, % | 4.85 | 5.35 | 5.61 |
| Crude Fiber, % | 2.19 | 2.12 | 2.10 |
| ME, kcal/Kg | 3054.00 | 3125.00 | 3165.00 |
| Lysine, % | 1.34 | 1.16 | 1.11 |
| Methionine, % | 0.63 | 0.51 | 0.51 |
| Threonine, % | 0.92 | 0.82 | 0.77 |
| Calcium, % | 0.92 | 0.85 | 0.80 |
| Phosphorus, % | 0.45 | 0.71 | 0.68 |
| Phosphorus, Available, % | 0.67 | 0.42 | 0.40 |
| Ca/P Ratio | 2.04 | 2.02 | 2.00 |
| Sodium, % | 0.21 | 0.20 | 0.20 |

Animal Information

Upon arrival all birds were vaccinated (by spray cabinet) with a commercially approved coccidia vaccine at the normal recommended dosage. Only healthy chicks were used in this study.

Housing

Chicks were raised in 5×5 feet (1.5 m×1.5 m) floor pens (stocking density of 1.0 $feet^2$ per bird) in a solid-sided barn, with concrete floors, and under ambient temperature control. At placement, birds were placed on reused litter homogenized from a previous necrotic enteritis study. Each pen contained 1 (one) tube feeder and six (6) nipple drinkers.

Body and Feed Weight

All birds were weighed by pen on DOT 0, 15, 35, and 42. The trial was terminated on DOT 42. On DOT 15 remaining starter feed was removed, weighed, and replaced with grower feed to DOT 35. On DOT 35 remaining grower feed was removed, weighed back, and replaced with finisher feed to DOT 42 (study termination).

Management

All birds were monitored for general flock condition, temperature, lighting, water, feed, litter condition, and unanticipated house conditions/events. Pens were checked daily for mortality. A gross necropsy was performed on all dead or culled birds to determine the bird sex and probable cause of death.

Data was analyzed using one-way ANOVA by the MIXED procedure of SAS for this complete randomized design. Cage served as the experimental unit. The statistical model included Cage weight gain, feed consumption, feed conversion, percent NE related mortality, and total percent mortality. All results were reported as least squares means. The significance level chosen was $\alpha=0.05$. Treatment effect was considered significant if $P<0.05$, whereas values between 0.05 P 0.10 were considered as statistical trends.

Results

No performance differences were observed between ground peppers inclusion rates (Table 6). Reused litter decreased ($P<0.05$) body weight gain and feed intake. Ground peppers tended to reduce feed intake at 15, 35, and 42 days of age compared to the no feed additive group. Body weight gain tended to increase at 15, 35, and 42 days of age compared to the control group, and feed conversion was reduced by 0.6 to 2.5% when ground peppers was added to the diets. No mortality differences were observed between birds fed ground peppers and the no feed additive group.

TABLE 6

| Summary 2016 SPRG NQPP102016 Ground peppers 2 levels and 2 litter types | | | | | | | | | |
|---|---|---|---|---|---|---|---|---|---|
| | Treatment | | | | | | | | |
| | Encapsulated | Encapsulated | | Encapsulated | Encapsulated | | | P-value | |
| Variable | ground pepper 0.15 Kg/ton | ground pepper 0.3 Kg/ton | Control | ground pepper 0.15 Kg/ton | ground pepper 0.3 Kg/ton | Control | PSE | Ground peppers | Litter |
| No. of Pens | 8 | 8 | 8 | 8 | 8 | 8 | | | |
| No. of Birds | 200 | 200 | 200 | 200 | 200 | 200 | | | |
| Litter Type | New | New | New | Reused | Reused | Reused | | | |
| Live performance, 15 d | | | | | | | | | |
| Feed consumption, Kg | 0.32 | 0.32 | 0.32 | 0.30 | 0.30 | 0.30 | 0.01 | 0.90 | 0.01 |
| Body weight gain, Kg | 0.33 | 0.32 | 0.32 | 0.31 | 0.30 | 0.29 | 0.01 | 0.24 | <.0001 |
| Feed Conversion | 1.11 | 1.14 | 1.15 | 1.15 | 1.16 | 1.16 | 0.04 | 0.54 | 0.27 |
| Live performance, 35 d | | | | | | | | | |
| Feed consumption, Kg | 2.90 | 2.88 | 2.90 | 2.72 | 2.72 | 2.72 | 0.03 | 0.93 | <.0001 |
| Body weight gain, Kg | 2.07 | 2.04 | 2.05 | 1.99 | 1.94 | 1.97 | 0.03 | 0.39 | 0.0004 |
| Feed Conversion | 1.43 (−1.4%) | 1.44 (−0.6%) | 1.45 | 1.39 (−1.4%) | 1.43 (−1.4%) | 1.41 | 0.01 | 0.11 | 0.003 |
| Live performance, 42 d | | | | | | | | | |
| Feed consumption, Kg | 4.01 | 4.06 | 4.09 | 3.91 | 3.87 | 3.87 | 0.05 | 0.88 | <.0001 |
| Body weight gain, Kg | 2.59 | 2.61 | 2.58 | 2.54 | 2.50 | 2.49 | 0.04 | 0.69 | 0.02 |
| Feed Conversion | 1.58 (−2.5%) | 1.58 (−2.5%) | 1.62 | 1.56 (−1.3%) | 1.57 (−0.6%) | 1.58 | 0.02 | 0.21 | 0.10 |
| Total Mortality % | 3.50 | 3.00 | 4.00 | 2.50 | 2.50 | 3.00 | 1.5 | 0.63 | 0.71 |

Example 3: Determine the Effect of Feeding Ground Peppers, Formulated Yeast and a Combination of Ground Peppers and Formulated Yeast to Broilers Challenged with *C. perfringens*

This study was conducted to evaluate the effects of ground peppers and formulated yeast fed to broilers challenged with *C. perfringens* (Table 7). A total of 2000 day-old male Ross×Ross chicks were obtained from a commercial hatchery. Chicks were vaccinated for Marek's and reovirus at the hatchery.

TABLE 7

| Experimental treatments | | | | | |
|---|---|---|---|---|---|
| Treatment | Test product | Starter DOT[1] 0-13 | Grower DOT 14-35 | Finisher DOT 14-35 | # of Pens |
| A | No Additive | None | DOT[1] 14 | None | 16 |
| B | Virginimycin | 20 g/ton | 20 g/ton | 20 g/ton | 16 |
| C | Formulated yeast | 0.5 lb/ton | 0.5 lb/ton | 0.5 lb/ton | 16 |
| D | Encapsulated ground pepper | 0.3 lb/ton | 0.3 lb/ton | 0.3 lb/ton | 16 |
| E | Encapsulated ground pepper + Formulated yeast | 0.3 lb/ton + 0.5 lb/ton | 0.3 lb/ton + 0.5 lb/ton | 0.3 lb/ton + 0.5 lb/ton | 16 |

[1]Day of hatch
Capsaicinoid content of encapsulated ground pepper is 0.5%

Experimental Diets

Feed consisted of non-medicated commercial-type broiler starter, grower, and finisher diets compounded according to meet or exceed NRC nutrient guidelines and contained feedstuffs commonly used in the United States (Table 8). Rations were fed ad libitum from date of chick arrival as follows: Starter—DOT 0 until DOT 15, grower DOT 15 to DOT 35, and finisher from DOT 35 to DOT 42 (study termination). Diets were fed as crumbles (starter feed) or pellets (grower and finisher feed). Pelleting of diets (grower and finisher diets) was manufactured with a California Pellet mill (at 80° C.). Experimental treatment feeds were prepared from a basal feed formulation.

TABLE 8

| Composition of the basal diet | | | |
|---|---|---|---|
| | Starter | Grower | Finisher |
| Ingredients, kg/ton | | | |
| Corn, Yellow Grain | 556.29 | 615.34 | 640.07 |
| Soybean Meal Dehulled, Solvent | 377.55 | 318.36 | 293.02 |
| Fat, Vegetable | 25.55 | 29.11 | 31.1 |
| Dicalcium Phosphate | 20.39 | 18.94 | 17.86 |
| Calcium Carbonate | 10.31 | 9.85 | 9.18 |
| Salt, (NaCl) | 4.61 | 4.39 | 4.41 |
| Methionine, MHA | 3.08 | 2.06 | 2.22 |
| L - LYSINE, 98.5% | 0.82 | 0.70 | 0.89 |
| Trace Mineral Premix | 0.75 | 0.70 | 0.75 |
| Vitamin Premix | 0.65 | 0.50 | 0.5 |
| Total | 1000.00 | 1000.00 | 1000.00 |
| Calculated Nutrients Composition | | | |
| Crude Protein, % | 22.45 | 20.0 | 19.0 |
| Fat, % | 4.85 | 5.35 | 5.61 |
| Crude Fiber, % | 2.19 | 2.12 | 2.10 |
| ME, kcal/Kg | 3054.00 | 3125.00 | 3165.00 |
| Lysine, % | 1.34 | 1.16 | 1.11 |
| Methionine, % | 0.63 | 0.51 | 0.51 |
| Threonine, % | 0.92 | 0.82 | 0.77 |
| Calcium, % | 0.92 | 0.85 | 0.80 |

TABLE 8-continued

| Composition of the basal diet | | | |
|---|---|---|---|
| | Starter | Grower | Finisher |
| Phosphorus, % | 0.45 | 0.71 | 0.68 |
| Phosphorus, Available, % | 0.67 | 0.42 | 0.40 |
| Ca/P Ratio | 2.04 | 2.02 | 2.00 |
| Sodium, % | 0.21 | 0.20 | 0.20 |

Animal Information

Upon arrival all birds were vaccinated (by spray cabinet) with a commercially approved coccidia vaccine at the normal recommended dosage. Only healthy chicks were used in this study.

Housing

Chicks were raised in 5×5 feet (1.5 m×1.5 m) floor pens (stocking density of 1.0 feet$^2$ per bird) in a solid-sided barn, with concrete floors, and under ambient temperature control. At placement, birds were placed on reused litter homogenized from a previous necrotic enteritis study. Each pen contained 1 (one) tube feeder and six (6) nipple drinkers.

*C. perfringens* Application

Feed in each pen had fifty (50) ml applied at 15 days of ~1×10$^8$ CFU/ml per pen of C.P #6.

Body and Feed Weight

All birds were weighed by pen on DOT 0, 15, 35, and 42. The trial was terminated on DOT 42. On DOT 15 remaining starter feed was removed, weighed, and replaced with grower feed to DOT 35. On DOT 35 remaining grower feed was removed, weighed back, and replaced with finisher feed to DOT 42 (study termination).

Management

All birds were monitored for general flock condition, temperature, lighting, water, feed, litter condition, and unanticipated house conditions/events. Pens were checked daily for mortality. A gross necropsy was performed on all dead or culled birds to determine the bird sex and probable cause of death.

Data was analyzed using one-way ANOVA by the MIXED procedure of SAS for this complete randomized design. Pen served as the experimental unit. The statistical model included pen weight gain, feed consumption, feed conversion, percent NE related mortality, and total percent mortality. All results were reported as least squares means. The significance level chosen was $\alpha=0.05$. Treatment effect was considered significant if $P<0.05$, whereas values between $0.05\leq P\leq 0.10$ were considered as statistical trends.

Broilers fed the combination of ground peppers and formulated yeast had a decreased (P<0.05) feed intake compared to birds fed the ground peppers (Table 9). Feed conversion tended (P=0.08) to decrease in birds fed the combination of ground peppers and formulated yeast compared to the ground peppers fed birds at 15 d of age. Body weight and FCR was numerically improved in birds fed the combination of ground peppers and formulated yeast compared to formulated yeast and ground peppers fed treatments. Necrotic enteritis related mortality was numerically lower for the combination feed treatment compared to the control and virginiamycin fed birds.

TABLE 9

Summary 2017 Ground peppers and Formulated Yeast Trial

| Variable | Control | Virginiamycin | Formulated yeast | Ground peppers | Ground peppers + Formulated yeast | PSE | P-value |
|---|---|---|---|---|---|---|---|
| | Treatment | | | | | | |
| No. of Pens | 16 | | | | | | |
| No. of Birds | 400 | | | | | | |
| Live performance, 15 d | | | | | | | |
| Feed consumption, Kg | $0.44^{ab}$ | $0.44^{ab}$ | $0.43^{ab}$ | $0.45^{a}$ | $0.41^{b}$ | 0.01 | 0.04 |
| Body weight gain, Kg | 0.37 | 0.38 | 0.37 | 0.37 | 0.37 | 0.01 | 0.63 |
| Feed Conversion | $1.35^{xy}$ | $1.32^{xy}$ | $1.32^{xy}$ | $1.38^{xy}$ | $1.23^{y}$ | 0.04 | 0.08 |
| Live performance, 35 d | | | | | | | |
| Feed consumption, Kg | 2.63 | 2.62 | 2.59 | 2.68 | 2.59 | 0.06 | 0.83 |
| Body weight gain, Kg | $1.61^{x}$ | $1.57^{xy}$ | $1.54^{y}$ | $1.57^{xy}$ | $1.60^{xy}$ | 0.02 | 0.08 |
| Feed Conversion | 1.69 | 1.73 | 1.73 | 1.77 | 1.67 | 0.05 | 0.31 |
| Live performance, 42 d | | | | | | | |
| Feed consumption, Kg | 3.87 | 3.70 | 3.85 | 3.87 | 3.81 | 0.09 | 0.63 |
| Body weight gain, Kg | 2.24 | 2.17 | 2.18 | 2.18 | 2.21 | 0.02 | 0.12 |
| Feed Conversion | 1.77 | 1.76 | 1.81 | 1.82 | 1.77 | 0.04 | 0.56 |
| Necrotic enteritis related mortality, % | 3.50 | 3.50 | 3.75 | 3.00 | 4.25 | 1.15 | 0.49 |
| Total Mortality % | 0.63 | 0.50 | 0.38 | 1.25 | 0.38 | 0.32 | 0.28 |

$^{a,b,c}$Means without a common superscript differ (P < 0.05)

$^{x,y}$Means without a common superscript tend to differ (P < 0.10)

Example 4: Determine the Effect of Feeding Ground Peppers at Four Inclusion Levels Fed in Combination with Formulated Yeast Challenged with *C. perfringens*

This study was conducted to evaluate the effects of ground peppers fed at four inclusion levels and formulated yeast fed to broilers challenged with *C. perfringens* (Table 10). A total of 3000 day-old male Ross×Ross chicks were obtained from a commercial hatchery. Chicks were vaccinated for Marek's and reovirus at the hatchery.

TABLE 10

Experimental treatments

| Treatment | Test product | Starter DOT[1] 0-15 | Grower DOT 15-28 | Finisher DOT 28-42 | # of Pens |
|---|---|---|---|---|---|
| A | No Additive | None | DOT[1] 14 | None | 20 |
| B | Virginimycin | 20 g/ton | 20 g/ton | 20 g/ton | 20 |
| C | Encapsulated ground pepper + Formulated yeast | 0.1 lb/ton + 0.50 lb/ton | 0.1 lb/ton + 0.50 lb/ton | 0.1 lb/ton + 0.50 lb/ton | 20 |
| D | Encapsulated ground pepper + Formulated yeast | 0.3 lb/ton + 0.50 lb/ton | 0.3 lb/ton + 0.50 lb/ton | 0.3 lb/ton + 0.50 lb/ton | 20 |
| E | Encapsulated ground pepper + Formulated yeast | 0.5 lb/ton + 0.50 lb/ton | 0.5 lb/ton + 0.50 lb/ton | 0.5 lb/ton + 0.50 lb/ton | 20 |
| F | Encapsulated ground pepper + Formulated yeast | 0.70 lb/ton + 0.50 lb/ton | 0.70 lb/ton + 0.50 lb/ton | 0.70 lb/ton + 0.50 lb/ton | 20 |

[1]Day of hatch

Capsaicinoid content of encapsulated ground pepper is 0.5%

Experimental Diets

Feed consisted of non-medicated commercial-type broiler starter, grower, and finisher diets compounded according to meet or exceed NRC nutrient guidelines and contained feedstuffs commonly used in the United States (Table 11). Rations were fed ad libitum from date of chick arrival as follows: Starter—DOT 0 until DOT 15, grower DOT 15 to DOT 28, and finisher from DOT 28 to DOT 42 (study termination). Diets were fed as crumbles (starter feed) or pellets (grower and finisher feed). Pelleting of diets (grower and finisher diets) was manufactured with a California Pellet mill (at 80° C.). Experimental treatment feeds were prepared from a basal feed formulation.

TABLE 11

Composition of the basal diet

| | Starter | Grower | Finisher |
|---|---|---|---|
| Ingredients, kg/ton | | | |
| Corn, Yellow Grain | 556.29 | 615.34 | 640.07 |
| Soybean Meal Dehulled, Solvent | 377.55 | 318.36 | 293.02 |
| Fat, Vegetable | 25.55 | 29.11 | 31.1 |
| Dicalcium Phosphate | 20.39 | 18.94 | 17.86 |
| Calcium Carbonate | 10.31 | 9.85 | 9.18 |
| Salt, (NaCl) | 4.61 | 4.39 | 4.41 |
| Methionine, MHA | 3.08 | 2.06 | 2.22 |
| L - LYSINE, 98.5% | 0.82 | 0.70 | 0.89 |
| Trace Mineral Premix | 0.75 | 0.70 | 0.75 |
| Vitamin Premix | 0.65 | 0.50 | 0.5 |
| Total | 1000.00 | 1000.00 | 1000.00 |
| Calculated Nutrients Composition | | | |
| Crude Protein, % | 22.45 | 20.0 | 19.0 |
| Fat, % | 4.85 | 5.35 | 5.61 |
| Crude Fiber, % | 2.19 | 2.12 | 2.10 |
| ME, kcal/Kg | 3054.00 | 3125.00 | 3165.00 |
| Lysine, % | 1.34 | 1.16 | 1.11 |
| Methionine, % | 0.63 | 0.51 | 0.51 |
| Threonine, % | 0.92 | 0.82 | 0.77 |
| Calcium, % | 0.92 | 0.85 | 0.80 |
| Phosphorus, % | 0.45 | 0.71 | 0.68 |
| Phosphorus, Available, % | 0.67 | 0.42 | 0.40 |
| Ca/P Ratio | 2.04 | 2.02 | 2.00 |
| Sodium, % | 0.21 | 0.20 | 0.20 |

Animal Information

Upon arrival all birds were vaccinated (by spray cabinet) with a commercially approved coccidia vaccine at the normal recommended dosage. Only healthy chicks were used in this study.

Housing

Chicks were raised in 5×5 feet (1.5 m×1.5 m) floor pens (stocking density of 1.0 feet$^2$ per bird) in a solid-sided barn, with concrete floors, and under ambient temperature control. At placement, birds were placed on reused litter homogenized from a previous necrotic enteritis study. Each pen contained 1 (one) tube feeder and six (6) nipple drinkers.

*C. perfringens Application*

Feed in each pen had fifty (50) ml applied at 15 days of ~1×10$^8$ CFU/ml per pen of C.P #6.

Body and Feed Weight

All birds were weighed by pen on DOT 0, 15, 35, and 42. The trial was terminated on DOT 42. On DOT 15 remaining starter feed was removed, weighed, and replaced with grower feed to DOT 35. On DOT 35 remaining grower feed was removed, weighed back, and replaced with finisher feed to DOT 42 (study termination).

Management

All birds were weighed by pen on DOT 0, 15, 28, and 42. The trial was terminated on DOT 42. On DOT 15 remaining starter feed was removed, weighed, and replaced with grower feed to DOT 28. On DOT 28 remaining grower feed was removed, weighed back, and replaced with finisher feed to DOT 42 (study termination).

Data was analyzed using one-way ANOVA by the MIXED procedure of SAS for this complete randomized design. Pen served as the experimental unit. The statistical model included pen weight gain, feed consumption, feed conversion, percent NE related mortality, and total percent mortality. All results were reported as least squares means. The significance level chosen was $\alpha=0.05$. Treatment effect was considered significant if $P<0.05$, whereas values between $0.05 \le P \le 0.10$ were considered as statistical trends.

Results

The combination of ground peppers and formulated yeast improved body weight gain, FCR and survivability (Table 12). Broilers fed the combination of ground peppers at 0.3 lb/ton finished feed and formulated yeast had a decreased ($P<0.05$) FCR at 15, 28 and 42 days of age compared to birds fed no feed additive. Body weight gain was increased ($P<0.05$) in birds fed the 0.3 lb ground peppers/ton plus formulated yeast compared to the control fed birds at 28 days of age. Birds fed the ground peppers at 0.7 lb/ton finished feed tended to have higher ($P=0.07$) feed intake compared to the 0.3 lb ground peppers/ton group. Total mortality was numerically reduced in birds fed all feed additives compared to the no feed additive fed group. These results suggest that feeding broilers ground peppers especially at the 0.3 lb/ton inclusion rate with formulated yeast is effective in controlling *C. perfringens* disease challenge.

TABLE 12

Summary 2017 SPRG NQPYC052017-48 Ground peppers and Formulated Yeast Trial

| | Treatment | | | | | | | |
|---|---|---|---|---|---|---|---|---|
| Variable | Control | Virginiamycin | Encapsulated ground pepper + Formulated yeast | Encapsulated ground pepper + Formulated yeast | Encapsulated ground pepper + Formulated yeast | Encapsulated ground pepper + Formulated yeast | PSE | P-value |
| No. of Pens | 20 | 20 | 20 | 20 | 20 | 20 | | |
| No. of Birds | 500 | 500 | 500 | 500 | 500 | 500 | | |
| Inclusion Rate | None | 20 g/ton | 0.10 + 0.50 lb/ton | 0.30 + 0.50 lb/ton | 0.50 + 0.50 lb/ton | 0.70 + 0.50 lb/ton | | |
| Live performance, 15 d | | | | | | | | |
| Feed consumption, Kg | 0.40 | 0.39 | 0.39 | 0.39 | 0.40 | 0.41 | 0.01 | 0.16 |
| Body weight gain, Kg | 0.32 | 0.33 | 0.32 | 0.33 | 0.33 | 0.33 | 0.01 | 0.23 |
| Feed Conversion | 1.40$^a$ | 1.33$^b$ | 1.35$^{ab}$ | 1.32$^b$ | 1.35$^{ab}$ | 1.36$^{ab}$ | 0.03 | 0.02 |

TABLE 12-continued

Summary 2017 SPRG NQPYC052017-48 Ground peppers and Formulated Yeast Trial

| | Treatment | | | | | | | |
|---|---|---|---|---|---|---|---|---|
| Variable | Control | Virginiamycin | Encapsulated ground pepper + Formulated yeast | Encapsulated ground pepper + Formulated yeast | Encapsulated ground pepper + Formulated yeast | Encapsulated ground pepper + Formulated yeast | PSE | P-value |
| Live performance, 35 d | | | | | | | | |
| Feed consumption, Kg | $1.76^{xy}$ | $1.73^{x}$ | $1.73^{x}$ | $1.74^{xy}$ | $1.73^{x}$ | $1.81^{y}$ | 0.03 | 0.06 |
| Body weight gain, Kg | $1.08^{a}$ | $1.10^{ab}$ | $1.07^{ab}$ | $1.12^{b}$ | $1.11^{ab}$ | $1.10^{ab}$ | 0.02 | 0.04 |
| Feed Conversion | $1.69^{a}$ | $1.62^{abc}$ | $1.66^{abc}$ | $1.59^{c}$ | $1.61^{bc}$ | $1.69^{a}$ | 0.04 | 0.003 |
| Live performance, 42 d | | | | | | | | |
| Feed consumption, Kg | $3.90^{xy}$ | $3.90^{xy}$ | $3.89^{xy}$ | $3.84^{x}$ | $3.90^{xy}$ | $3.98^{y}$ | 0.04 | 0.07 |
| Body weight gain, Kg | 2.21 | 2.27 | 2.22 | 2.27 | 2.29 | 2.27 | 0.03 | 0.12 |
| Feed Conversion | $1.79^{a}$ | $1.74^{abc}$ | $1.78^{b}$ | $1.72^{c}$ | $1.73^{bc}$ | $1.77^{abc}$ | 0.02 | 0.005 |
| Total Mortality % | 6.29 | 5.36 | 5.40 | 3.60 | 4.80 | 5.00 | 1.49 | 0.61 |

$^{a,b,c}$Means without a common superscript differ ($P < 0.05$)
$^{x,y}$Means without a common superscript tend to differ ($P < 0.10$)

Example 5: Determine the Effect of Feeding *Capsicum* Product, Formulated Yeast and *Bacillus licheniformis* to Broilers Challenged with *E. maxima* and *C. perfringens*

A total of 256-day-old male Cobb×Cobb chicks were obtained from a commercial hatchery. Chicks were vaccinated for Marek's disease and reovirus at the hatchery. The birds were randomly assigned to 32 battery cages with eight chicks per cage. A total of four treatments (Table 13) were allotted resulting in eight pens per treatment. Temperature and lighting were adjusted according to the husbandry guidelines of the Cobb broiler (Cobb, 2012). Each cage was equipped with a feed and water trough. Water and feed were provided ad libitum. A 22.5% crude protein corn soybean-based diet (Table 14) was fed through 28-d posthatching. The diet was representative of a local commercial formulation and calculated analyses met or exceeded NRC broiler starter requirements. Experimental treatment feeds were prepared from this non-medicated basal starter feed.

Bird Allocation and Cage Randomization

Cages were blocked by location in the battery. The study began when the birds were placed (day of hatch) (DOT 0) at which time they were allocated to the experimental cages. No birds were replaced during the course of the study.

Cage Weights

All birds were weighed on DOT 0, 14, 21, and 28. Feed was weighed on DOT 0 and remaining feed was weighed on DOT 14, 21, and 28.

Disease Induction

On DOT 14, all birds were orally inoculated with ~5,000 oocysts of *E. maxima*. Starting on DOT 19, all birds, except Treatment 1 (Control) were given a broth culture of *C. perfringens* ~108 cfu/ml. The birds were administered a fresh broth culture once daily for 3 days (on DOTs 19, 20, and 21).

Necrotic Enteritis Intestinal Lesion Scoring

On DOT 21, three birds from each cage were selected, sacrificed, weighed, and examined for the degree of presence of Necrotic Enteritis lesions. If less than three birds were present at time of scoring, all remaining birds within the cage were scored. The scoring was based on a 0 to 3 score, with 0 being normal and 3 being the most severe. (Hofacre et. al, 1998)

Management

The facility was checked at least twice daily to assure that all cages had water and that feed was available in every cage. The building temperature's range was maintained at an appropriate temperature for the age of the birds, and continuous light was provided by fluorescent lamps hung vertically along the wall. Feed and water were given ad libitum. When mortality birds were removed from cages, the cage number, date, weight of the bird, sex, and probable cause of death were recorded.

Data analysis

Data was analyzed using one-way ANOVA by the MIXED procedure of SAS for this complete randomized design. Cage served as the experimental unit. The statistical model included cage weight gain, feed consumption, feed conversion, necrotic enteritis lesion scores, and % necrotic enteritis related mortality were calculated. All results were reported as least squares means. The significance level chosen was $\alpha=0.05$. Treatment effect was considered significant if $P<0.05$, whereas values between $0.05 \leq P \leq 0.10$ were considered as statistical trends.

Summary

Broilers fed the combination of *Capsicum* Product, formulated yeast and *B. licheniformis* had similar ($P>0.10$) FCR to 21 days of age as the unchallenged no feed additive treatment group. Broilers fed the combination of *Capsicum* Product, formulated yeast and *B. licheniformis* and BMD had decreased ($P<0.05$) FCR during the challenge and post challenge periods (d 14-28) compared to the challenge control birds (Table 15). Overall FCR was reduced ($P<0.05$) in birds fed BMD and the combination products compared to the challenged no feed additive control. Birds fed the combination of *Capsicum* Product, formulated yeast and *B. licheniformis* had similar ($P>0.10$) d 1-28 FCR to the unchallenged control group. Body weight gain was not impacted by either the BMD or combination treatment compared to the challenged no feed additive control group. No differences were noted in feed intake between all treatments. Necrotic enteritis lesion scores and necrotic enteritis related mortality were lower ($P<0.05$) in birds fed BMD and *Capsicum* Product, formulated yeast and *B. licheniformis* treatment combination compared to the challenged control birds. The data indicates that the treatment combination of *Capsicum* Product, formulated yeast and *B. licheniformis* and BMD are effective in controlling *C. perfringens* disease challenge.

TABLE 13

| Experimental treatments | | | | | |
|---|---|---|---|---|---|
| Treatment | Testing Product | Conc. of Testing Product | *E. maxima* Challenge | *C. perfringens* Challenge | # of Cages |
| A | No Additive | None | DOT[1] 14 | None | 8 |
| B | No Additive | None | DOT 14 | DOT 19, 20, and 21 | 8 |
| C | BMD | 50.0 g/ton | DOT 14 | DOT 19, 20, and 21 | 8 |
| D | Capsicum Product + formulated yeast + *B. licheniformis* | 0.30 lb/ton + 0.5 lb/ton + 3 × $10^5$ cfu/g in final feed | DOT 14 | DOT 19, 20, and 21 | 8 |

[1]Day of hatch

TABLE 1.14

| Composition of the basal diet[1] | |
|---|---|
| Ingredients | Kg/ton |
| Corn, Yellow Grain | 556.29 |
| Soybean Meal Dehulled, Solvent | 377.55 |
| Fat, Vegetable | 25.55 |
| Dicalcium Phosphate | 20.39 |
| Calcium Carbonate | 10.31 |
| Salt, (NaCl) | 4.61 |
| Methionine, MHA | 3.08 |
| L - LYSINE, 98.5% | 0.82 |
| Trace Mineral Premix | 0.75 |
| Vitamin Premix | 0.65 |
| Total | 1000.00 |

TABLE 1.14-continued

| Composition of the basal diet[1] | |
|---|---|
| Ingredients | Kg/ton |
| Calculated Nutrients Composition | |
| Crude Protein, % | 22.45 |
| Fat, % | 4.85 |
| Crude Fiber, % | 2.19 |
| ME, kcal/Kg | 3054.00 |
| Lysine, % | 1.34 |
| Methionine, % | 0.63 |
| Threonine, % | 0.92 |
| Calcium, % | 0.92 |
| Phosphorus, % | 0.45 |
| Phosphorus, Available, % | 0.67 |
| Ca/P Ratio | 2.04 |
| Sodium, % | 0.21 |

[1]Basal diet was prepared by Southern Poultry Research

TABLE 15

| Summary 2018 SPRG NQ NE0218 Trial | | | | |
|---|---|---|---|---|
| | Treatment | | | |
| Variable | Non Challenged Control | Challenged Control | BMD | *Capsicum* Product + formulated yeast + *B. licheniformis* |
| No. of Cages | 8 | 8 | 8 | 8 |
| No. of Birds | 64 | 64 | 64 | 64 |
| *C. Perfringens* Challenge | − | + | + | + |
| Live performance, 0-21 d | | | | |
| Feed consumption, Kg | 0.96 | 0.95 | 0.94 | 0.92 |
| Body weight gain, Kg | 0.57[a] | 0.51[b] | 0.52[ab] | 0.52[ab] |
| Feed Conversion | 1.69[b] | 1.85[a] | 1.81[a] | 1.76[ab] |
| Live performance, 14-21 d | | | | |
| Feed consumption, Kg | 0.50 | 0.51 | 0.49 | 0.48 |
| Body weight gain, Kg | 0.31[a] | 0.26[b] | 0.28[b] | 0.26[b] |
| Feed Conversion | 1.62[c] | 1.98[a] | 1.77[b] | 1.81[b] |
| Live performance, 14-28 d | | | | |
| Feed consumption, Kg | 0.90 | 1.08 | 0.91 | 0.92 |
| Body weight gain, Kg | 0.58 | 0.53 | 0.53 | 0.51 |
| Feed Conversion | 1.56[c] | 2.04[a] | 1.73[bc] | 1.79[b] |
| Live performance, 0-28 d | | | | |
| Feed consumption, Kg | 1.37 | 1.50 | 1.37 | 1.35 |
| Body weight gain, Kg | 0.84 | 0.79 | 0.77 | 0.77 |
| Feed Conversion | 1.63[c] | 1.90[a] | 1.78[b] | 1.75[bc] |
| Necrotic enteritis lesion score | 0.0[c] | 0.9[a] | 0.5[b] | 0.4[b] |

TABLE 15-continued

| Summary 2018 SPRG NQ NE0218 Trial | | | | |
|---|---|---|---|---|
| | Treatment | | | |
| Variable | Non Challenged Control | Challenged Control | BMD | *Capsicum* Product + formulated yeast + *B. licheniformis* |
| Necrotic enteritis related mortality, % | $0^b$ | $11^a$ | $2^b$ | $3^b$ |

[a,b,c]Means within a row with no common superscripts differ significantly (P < 0.05)

Example 6: Determine the Effect of Feeding Antimicrobial Clay and *Bacillus licheniformis* to Broilers Challenged with *E. maxima* and *C. perfringens*

A total of 256-day-old male Cobb×Cobb chicks were obtained from a commercial hatchery. Chicks were vaccinated for Marek's disease and reovirus at the hatchery. The birds were randomly assigned to 32 battery cages with eight chicks per cage. A total of four treatments (Table 16) were allotted resulting in eight pens per treatment. Temperature and lighting were adjusted according to the husbandry guidelines of the Cobb broiler (Cobb, 2012). Each cage was equipped with a feed and water trough. Water and feed were provided ad libitum. A 22.5% crude protein corn soybean-based diet (Table 17) through 28-d posthatching. The diet was representative of a local commercial formulation and calculated analyses met or exceeded NRC broiler starter requirements. Experimental treatment feeds were prepared from this non-medicated basal starter feed.

Bird Allocation and Cage Randomization

Cages were blocked by location in the battery. The study began when the birds were placed (day of hatch) (DOT 0) at which time they were allocated to the experimental cages. No birds were replaced during the course of the study.

Cage Weights

All birds were weighed on DOT 0, 14, 21, and 28. Feed was weighed on DOT 0 and remaining feed was weighed on DOT 14, 21, and 28.

Disease Induction

On DOT 14, all birds were orally inoculated with ~5,000 oocysts of *E. maxima.*

Starting on DOT 19, all birds, except Treatment 1 (Control) were given a broth culture of *C. perfringens* ~$10^8$ cfu/ml. The birds were administered a fresh broth culture once daily for 3 days (on DOTs 19, 20, and 21).

Necrotic Enteritis Intestinal Lesion Scoring

On DOT 21, three birds from each cage were selected, sacrificed, weighed, and examined for the degree of presence of Necrotic Enteritis lesions. If less than three birds were present at time of scoring, all remaining birds within the cage were scored. The scoring was based on a 0 to 3 score, with 0 being normal and 3 being the most severe. (Hofacre et. al, 1998)

Management

The facility was checked at least twice daily to assure that all cages had water and that feed was available in every cage. The birds were watched closely for any abnormal conditions. The building temperature's range was maintained at an appropriate temperature for the age of the birds. Even, continuous light was provided by fluorescent lamps hung vertically along the wall. Feed and water were given ad libitum. When mortality birds were removed from cages, the cage number, date, weight of the bird, sex, and probable cause of death were recorded.

Data was analyzed using one-way ANOVA by the MIXED procedure of SAS for this complete randomized design. Cage served as the experimental unit. The statistical model included cage weight gain, feed consumption, feed conversion, necrotic enteritis lesion scores, and % necrotic enteritis related mortality were calculated. All results were reported as least squares means. The significance level chosen was $\alpha=0.05$. Treatment effect was considered significant if $P<0.05$, whereas values between $0.05 \leq P \leq 0.10$ were considered as statistical trends.

Summary

Broilers fed the combination of Antimicrobial Clay and *B. licheniformis* and BMD had increased (P<0.05) body weight gain and decreased (P<0.05) FCR during the challenge and post challenge periods (d 14-28) compared to the challenge control birds (Table 18). Similarly, overall (d 0-28) FCR was reduced and body weight gain was increased in birds fed the Antimicrobial Clay and *B. licheniformis* combination and BMD compared to the challenged control birds and similar (P>0.10) FCR and body weight gain to the unchallenged control group.

Necrotic enteritis lesion score was lower (P<0.05) in birds fed the Antimicrobial Clay and *B. licheniformis* combination treatment and BMD compared to the challenged control birds. Birds fed the BMD feed treatment had lower (P<0.05) necrotic enteritis mortality compared to the challenged control group. Birds fed Antimicrobial Clay and *B. licheniformis* had similar (P>0.10) mortality compared to the BMD and challenged control groups. The data suggests that both the combination Antimicrobial Clay and *B. licheniformis* product and BMD were effective in controlling *C. perfringens* disease challenge.

TABLE 16

| Experimental treatments | | | | | |
|---|---|---|---|---|---|
| Treatment | Testing Product | Conc. of Testing Product | *E. maxima* Challenge | *C. perfringens* Challenge | # of Cages |
| A | No Additive | None | DOT[1] 14 | None | 8 |
| B | No Additive | None | DOT 14 | DOT 19, 20, and 21 | 8 |
| C | BMD | 50.0 g/ton | DOT 14 | DOT 19, 20, and 21 | 8 |

TABLE 16-continued

| Experimental treatments | | | | | |
|---|---|---|---|---|---|
| Treatment | Testing Product | Conc. of Testing Product | *E. maxima* Challenge | *C. perfringens* Challenge | # of Cages |
| D | Antimicrobial Clay + *B. licheniformis* | 4.0 lb/ton + 3 × $10^5$ cfu/g in final feed | DOT 14 | DOT 19, 20, and 21 | 8 |

[1]Day of hatch

TABLE 17

| Composition of the basal diet[1] | |
|---|---|
| Ingredients | Kg/ton |
| Corn, Yellow Grain | 556.29 |
| Soybean Meal Dehulled, Solvent | 377.55 |
| Fat, Vegetable | 25.55 |
| Dicalcium Phosphate | 20.39 |
| Calcium Carbonate | 10.31 |
| Salt, (NaCl) | 4.61 |
| Methionine, MHA | 3.08 |
| L - LYSINE, 98.5% | 0.82 |
| Trace Mineral Premix | 0.75 |
| Vitamin Premix | 0.65 |
| Total | 1000.00 |

TABLE 17-continued

| Composition of the basal diet[1] | |
|---|---|
| Ingredients | Kg/ton |
| Calculated Nutrients Composition | |
| Crude Protein, % | 22.45 |
| Fat, % | 4.85 |
| Crude Fiber, % | 2.19 |
| ME, kcal/Kg | 3054.00 |
| Lysine, % | 1.34 |
| Methionine, % | 0.63 |
| Threonine, % | 0.92 |
| Calcium, % | 0.92 |
| Phosphorus, % | 0.45 |
| Phosphorus, Available, % | 0.67 |
| Ca/P Ratio | 2.04 |
| Sodium, % | 0.21 |

[1]Basal diet was prepared by Southern Poultry Research

TABLE 18

| Summary 2018 SPRG NQ NE0718 Trial | | | | |
|---|---|---|---|---|
| | Treatment | | | |
| Variable | Non Challenged Control | Challenged Control | BMD | Antimicrobial Clay + *B. licheniformis* |
| No. of Cages | 8 | 8 | 8 | 8 |
| No. of Birds | 64 | 64 | 64 | 64 |
| *C. Perfringens* Challenge | − | + | + | + |
| Live performance, 0-21 d | | | | |
| Feed consumption, Kg | 0.86 | 0.93 | 0.87 | 0.88 |
| Body weight gain, Kg | 0.56[a] | 0.51[b] | 0.57[a] | 0.55[ab] |
| Feed Conversion | 1.53[c] | 1.82[a] | 1.53[c] | 1.61[bc] |
| Live performance, 14-21 d | | | | |
| Feed consumption, Kg | 0.52 | 0.51 | 0.55 | 0.55 |
| Body weight gain, Kg | 0.34[a] | 0.24[c] | 0.32[ab] | 0.30[b] |
| Feed Conversion | 1.53[c] | 2.12[a] | 1.72[b] | 1.82[b] |
| Live performance, 14-28 d | | | | |
| Feed consumption, Kg | 0.87[a] | 0.79[b] | 0.98[a] | 0.92[a] |
| Body weight gain, Kg | 0.56[a] | 0.38[b] | 0.56[a] | 0.53[a] |
| Feed Conversion | 1.56[c] | 2.09[a] | 1.75[b] | 1.73[b] |
| Live performance, 0-28 d | | | | |
| Feed consumption, Kg | 1.21 | 1.19 | 1.30 | 1.26 |
| Body weight gain, Kg | 0.78[a] | 0.64[b] | 0.81[a] | 0.79[a] |
| Feed Conversion | 1.55[b] | 1.86[a] | 1.60[b] | 1.60[b] |
| Necrotic enteritis lesion score | 0.00[c] | 1.17[a] | 0.79[b] | 0.58[b] |

TABLE 18-continued

| Summary 2018 SPRG NQ NE0718 Trial | | | | |
|---|---|---|---|---|
| | Treatment | | | |
| Variable | Non Challenged Control | Challenged Control | BMD | Antimicrobial Clay + *B. licheniformis* |
| Necrotic enteritis related mortality, % | $0.0^{b}$ | $4.7^{a}$ | $0.0^{b}$ | $1.56^{ab}$ |

$^{a,b,c}$Means within a row with no common superscripts differ significantly (P < 0.05)

Example 7: Determine the Effect of Feeding *Capsicum* Product and *Bacillus licheniformis* to Broilers Challenged with *E. maxima* and *C. perfringens*

A total of 256-day-old male Cobb×Cobb chicks were obtained from a commercial hatchery. Chicks were vaccinated for Marek's disease and reovirus at the hatchery. The birds were randomly assigned to 32 battery cages with eight chicks per cage. A total of four treatments (Table 19) were allotted resulting in eight pens per treatment. Temperature and lighting were adjusted according to the husbandry guidelines of the Cobb broiler (Cobb, 2012). Each cage was equipped with a feed and water trough. Water and feed were provided ad libitum. A 22.5% crude protein corn soybean-based diet (Table 20) through 28-d posthatching. The diet was representative of a local commercial formulation and calculated analyses met or exceeded NRC broiler starter requirements. Experimental treatment feeds were prepared from this non-medicated basal starter feed.

Bird Allocation and Cage Randomization

Cages were blocked by location in the battery. The study began when the birds were placed (day of hatch) (DOT 0) at which time they were allocated to the experimental cages. No birds were replaced during the course of the study.

Cage Weights

All birds were weighed on DOT 0, 14, 21, and 28. Feed was weighed on DOT 0 and remaining feed was weighed on DOT 14, 21, and 28.

Disease Induction

On DOT 14, all birds were orally inoculated with ~5,000 oocysts of *E. maxima.*

Starting on DOT 19, all birds, except Treatment 1 (Control) were given a broth culture of *C. perfringens* ~$10^{8}$ cfu/ml. The birds were administered a fresh broth culture once daily for 3 days (on DOTs 19, 20, and 21).

Necrotic Enteritis Intestinal Lesion Scoring

On DOT 21, three birds from each cage were selected, sacrificed, weighed, and examined for the degree of presence of Necrotic Enteritis lesions. If less than three birds were present at time of scoring, all remaining birds within the cage were scored. The scoring was based on a 0 to 3 score, with 0 being normal and 3 being the most severe. (Hofacre et. al, 1998)

Management

The facility was checked at least twice daily to assure that all cages had water and that feed was available in every cage. The birds were watched closely for any abnormal conditions. The building temperature's range was maintained at an appropriate temperature for the age of the birds. Even, continuous light was provided by fluorescent lamps hung vertically along the wall. Feed and water were given ad libitum. When mortality birds were removed from cages, the cage number, date, weight of the bird, sex, and probable cause of death were recorded.

Data was analyzed using one-way ANOVA by the MIXED procedure of SAS for this complete randomized design. Cage served as the experimental unit. The statistical model included cage weight gain, feed consumption, feed conversion, necrotic enteritis lesion scores, and % necrotic enteritis related mortality were calculated. All results were reported as least squares means. The significance level chosen was $\alpha=0.05$. Treatment effect was considered significant if $P<0.05$, whereas values between $0.05 \leq P \leq 0.10$ were considered as statistical trends.

Summary

Broilers fed the combination of *Capsicum* Product and *B. licheniformis* and BMD had increased (P<0.05) body weight gain and decreased (P<0.05) FCR during the challenge and post challenge periods (d 14-28) compared to the challenge control birds (Table 21). Similarly, overall (d 0-28) body weight gain was increased in birds fed BMD compared to the challenged control birds and similar (P>0.10) to the unchallenged control group. Broilers fed the combination of *Capsicum* Product and *B. licheniformis* had increased (P<0.05) body weight gain compared to the challenged no feed additive group.

Necrotic enteritis lesion score was lower (P<0.05) in birds fed the *Capsicum* Product and *B. licheniformis* combination treatment and BMD compared to the challenged control birds. No differences (P<0.10) necrotic enteritis mortality were noted. The data suggests that both the combination *Capsicum* Product and *B. licheniformis* product and BMD were effective in controlling *C. perfringens* disease challenge.

TABLE 19

| Experimental treatments | | | | | |
|---|---|---|---|---|---|
| Treatment | Testing Product | Conc. of Testing Product | *E. maxima* Challenge | *C. perfringens* Challenge | # of Cages |
| A | No Additive | None | DOT[1] 14 | None | 8 |
| B | No Additive | None | DOT 14 | DOT 19, 20, and 21 | 8 |
| C | BMD | 50.0 g/ton | DOT 14 | DOT 19, 20, and 21 | 8 |

TABLE 19-continued

| Experimental treatments | | | | | |
|---|---|---|---|---|---|
| Treatment | Testing Product | Conc. of Testing Product | *E. maxima* Challenge | *C. perfringens* Challenge | # of Cages |
| D | *Capsicum* Product + *B. licheniformis* | 0.3 lb/ton + 3 × $10^5$ cfu/g in final feed | DOT 14 | DOT 19, 20, and 21 | 8 |

[1]Day of hatch

TABLE 20

| Composition of the basal diet[1] | |
|---|---|
| Ingredients | Kg/ton |
| Corn, Yellow Grain | 556.29 |
| Soybean Meal Dehulled, Solvent | 377.55 |
| Fat, Vegetable | 25.55 |
| Dicalcium Phosphate | 20.39 |
| Calcium Carbonate | 10.31 |
| Salt, (NaCl) | 4.61 |
| Methionine, MHA | 3.08 |
| L - LYSINE, 98.5% | 0.82 |
| Trace Mineral Premix | 0.75 |
| Vitamin Premix | 0.65 |
| Total | 1000.00 |

TABLE 20-continued

| Composition of the basal diet[1] | |
|---|---|
| Ingredients | Kg/ton |
| Calculated Nutrients Composition | |
| Crude Protein, % | 22.45 |
| Fat, % | 4.85 |
| Crude Fiber, % | 2.19 |
| ME, kcal/Kg | 3054.00 |
| Lysine, % | 1.34 |
| Methionine, % | 0.63 |
| Threonine, % | 0.92 |
| Calcium, % | 0.92 |
| Phosphorus, % | 0.45 |
| Phosphorus, Available, % | 0.67 |
| Ca/P Ratio | 2.04 |
| Sodium, % | 0.21 |

[1]Basal diet was prepared by Southern Poultry Research

TABLE 21

| Summary 2018 SPRG NQ NE0818 Trial | | | | |
|---|---|---|---|---|
| | Treatment | | | |
| Variable | Non Challenged Control | Challenged Control | BMD | *Capsicum* Product + *B. licheniformis* |
| No. of Cages | 8 | 8 | 8 | 8 |
| No. of Birds | 64 | 64 | 64 | 64 |
| *C. Perfringens* Challenge | − | + | + | + |
| Live performance, 0-21 d | | | | |
| Feed consumption, Kg | 1.04 | 0.94 | 1.07 | 1.01 |
| Body weight gain, Kg | $0.72^{a}$ | $0.54^{b}$ | $0.66^{a}$ | $0.60^{b}$ |
| Feed Conversion | $1.45^{b}$ | $1.74^{a}$ | $1.62^{ab}$ | $1.69^{a}$ |
| Live performance, 14-21 d | | | | |
| Feed consumption, Kg | 0.59 | 0.52 | 0.58 | 0.54 |
| Body weight gain, Kg | $0.39^{a}$ | $0.21^{c}$ | $0.30^{b}$ | $0.27^{b}$ |
| Feed Conversion | $1.52^{c}$ | $2.47^{a}$ | $1.95^{b}$ | $2.01^{b}$ |
| Live performance, 14-28 d | | | | |
| Feed consumption, Kg | 0.99 | 0.87 | 1.08 | 0.97 |
| Body weight gain, Kg | $0.63^{a}$ | $0.39^{c}$ | $0.56^{ab}$ | $0.50^{b}$ |
| Feed Conversion | $1.57^{c}$ | $2.23^{a}$ | $1.93^{b}$ | $1.94^{b}$ |
| Live performance, | | | | |

TABLE 21-continued

Summary 2018 SPRG NQ NE0818 Trial

| Variable | Non Challenged Control | Challenged Control | BMD | *Capsicum* Product + *B. licheniformis* |
|---|---|---|---|---|
| | Treatment | | | |
| 0-28 d | | | | |
| Feed consumption, Kg | 1.43 | 1.27 | 1.54 | 1.42 |
| Body weight gain, Kg | $0.96^{a}$ | 0.72° | $0.92^{ab}$ | $0.83^{b}$ |
| Feed Conversion | $1.49^{b}$ | $1.77^{a}$ | $1.67^{a}$ | $1.71^{a}$ |
| Necrotic enteritis lesion score | $0.00^{c}$ | $1.04^{a}$ | $0.50^{b}$ | $0.42^{b}$ |
| Necrotic enteritis related mortality, % | 0.0 | 1.6 | 0.0 | 0.0 |

$^{a,b,c}$Means within a row with no common superscripts differ significantly ($P < 0.05$)

Example 8: Determine the Effect of Feeding Formulated Yeast and *Bacillus licheniformis* to Broilers Challenged with *E. maxima* and *C. perfringens*

A total of 256-day-old male Cobb×Cobb chicks were obtained from a commercial hatchery. Chicks were vaccinated for Marek's and reovirus at the hatchery. The birds were randomly assigned to 32 battery cages with eight chicks per cage. A total of four treatments (Table 22) were allotted resulting in eight pens per treatment. Temperature and lighting were adjusted according to the husbandry guidelines of the Cobb broiler (Cobb, 2012). Each cage was equipped with a feed and water trough. Water and feed were provided ad libitum. A 22.5% crude protein corn soybean-based diet (Table 23) through 28-d posthatching. The diet was representative of a local commercial formulation and calculated analyses met or exceeded NRC broiler starter requirements. Experimental treatment feeds were prepared from this non-medicated basal starter feed.

Bird Allocation and Cage Randomization

Cages were blocked by location in the battery. The study began when the birds were placed (day of hatch) (DOT 0) at which time they were allocated to the experimental cages. No birds were replaced during the course of the study.

Cage Weights

All birds were weighed on DOT 0, 14, 21, and 28. Feed was weighed on DOT 0 and remaining feed was weighed on DOT 14, 21, and 28.

Disease Induction

On DOT 14, all birds were orally inoculated with ~5,000 oocysts of *E. maxima.*

Starting on DOT 19, all birds, except Treatment 1 (Control) were given a broth culture of *C. perfringens* ~$10^{8}$ cfu/ml. The birds were administered a fresh broth culture once daily for 3 days (on DOTs 19, 20, and 21).

Necrotic Enteritis Intestinal Lesion Scoring

On DOT 21, three birds from each cage were selected, sacrificed, weighed, and examined for the degree of presence of Necrotic Enteritis lesions. If less than three birds were present at time of scoring, all remaining birds within the cage were scored. The scoring was based on a 0 to 3 score, with 0 being normal and 3 being the most severe. (Hofacre et. al, 1998)

Management

The facility was checked at least twice daily to assure that all cages had water and that feed was available in every cage. The birds were watched closely for any abnormal conditions. The building temperature's range was maintained at an appropriate temperature for the age of the birds. Even, continuous light was provided by fluorescent lamps hung vertically along the wall. Feed and water were given ad libitum. When mortality birds were removed from cages, the cage number, date, weight of the bird, sex, and probable cause of death were recorded.

Data was analyzed using one-way ANOVA by the MIXED procedure of SAS for this complete randomized design. Cage served as the experimental unit. The statistical model included cage weight gain, feed consumption, feed conversion, necrotic enteritis lesion scores, and % necrotic enteritis related mortality were calculated. All results were reported as least squares means. The significance level chosen was $\alpha=0.05$. Treatment effect was considered significant if $P<0.05$, whereas values between $0.05 \leq P \leq 0.10$ were considered as statistical trends.

Summary

Broilers fed the combination of formulated yeast and *B. licheniformis* had increased ($P<0.05$) body weight gain and decreased ($P<0.05$) FCR during the challenge and post challenge periods (d 14-28) compared to the challenge control birds (Table 24). During this period birds fed BMD had similar body weight gains and decreased ($P<0.05$) FCR compared to the challenged control. Overall (d 0-28) FCR was decreased ($P<0.05$) in birds fed the combination of formulated yeast and *B. licheniformis* and BMD compared to the challenged control birds and similar to the unchallenged group. Birds fed the combination of formulated yeast and *B. licheniformis* had similar ($P>0.10$) FCR and body weight gain to the unchallenged control group during d 0-21 and d 14-21 periods. Birds fed BMD had similar body weight gain to the unchallenged control during the d 0-21 period.

Necrotic enteritis lesion score was lower ($P<0.05$) in birds fed the formulated yeast and *B. licheniformis* combination treatment and BMD compared to the challenged control birds. While birds fed BMD had similar ($P<0.10$) necrotic enteritis lesion score as the unchallenged control group. The unchallenged control, BMD and the combination formulated yeast and *B. licheniformis* treatments had decreased ($P<0.05$) necrotic enteritis mortality compared to the challenged control group. The data suggests that both the combination formulated yeast and *B. licheniformis* product and BMD were effective in controlling *C. perfringens* disease challenge.

TABLE 22

| Experimental treatments | | | | | |
|---|---|---|---|---|---|
| Treatment | Testing Product | Conc. of Testing Product | *E. maxima* Challenge | *C. perfringens* Challenge | # of Cages |
| A | No Additive | None | DOT[1] 14 | None | 8 |
| B | No Additive | None | DOT 14 | DOT 19, 20, and 21 | 8 |
| C | BMD | 50.0 g/ton | DOT 14 | DOT 19, 20, and 21 | 8 |
| D | Formulated yeast + *B. licheniformis* | 0.5 lb/ton + 3 × $10^5$ cfu/g in final feed | DOT 14 | DOT 19, 20, and 21 | 8 |

[1]Day of hatch

TABLE 23

| Composition of the basal diet[1] | |
|---|---|
| Ingredients | Kg/ton |
| Corn, Yellow Grain | 556.29 |
| Soybean Meal Dehulled, Solvent | 377.55 |
| Fat, Vegetable | 25.55 |
| Dicalcium Phosphate | 20.39 |
| Calcium Carbonate | 10.31 |
| Salt, (NaCl) | 4.61 |
| Methionine, MHA | 3.08 |
| L - LYSINE, 98.5% | 0.82 |
| Trace Mineral Premix | 0.75 |
| Vitamin Premix | 0.65 |
| Total | 1000.00 |

TABLE 23-continued

| Composition of the basal diet[1] | |
|---|---|
| Ingredients | Kg/ton |
| Calculated Nutrients Composition | |
| Crude Protein, % | 22.45 |
| Fat, % | 4.85 |
| Crude Fiber, % | 2.19 |
| ME, kcal/Kg | 3054.00 |
| Lysine, % | 1.34 |
| Methionine, % | 0.63 |
| Threonine, % | 0.92 |
| Calcium, % | 0.92 |
| Phosphorus, % | 0.45 |
| Phosphorus, Available, % | 0.67 |
| Ca/P Ratio | 2.04 |
| Sodium, % | 0.21 |

[1]Basal diet was prepared by Southern Poultry Research

TABLE 24

| Summary 2018 SPRG NQ NE0716 Trial | | | | |
|---|---|---|---|---|
| | Treatment | | | |
| Variable | Non Challenged Control | Challenged Control | BMD | Formulated yeast + *B. licheniformis* |
| No. of Cages | 8 | 8 | 8 | 8 |
| No. of Birds | 64 | 64 | 64 | 64 |
| *C. Perfringens* Challenge | − | + | + | + |
| Live performance, 0-21 d | | | | |
| Feed consumption, Kg | 0.71 | 0.70 | 0.75 | 0.74 |
| Body weight gain, Kg | $0.36^a$ | $0.28^b$ | $0.34^a$ | $0.36^a$ |
| Feed Conversion | $1.97^c$ | $2.49^a$ | $2.21^b$ | $2.06^{bc}$ |
| Live performance, 14-21 d | | | | |
| Feed consumption, Kg | 0.34 | 0.35 | 0.34 | 0.33 |
| Body weight gain, Kg | $0.18^a$ | $0.13^c$ | $0.15^{bc}$ | $0.16^{ab}$ |
| Feed Conversion | $1.90^c$ | $2.68^a$ | $2.30^b$ | $2.08^{bc}$ |
| Live performance, 14-28 d | | | | |
| Feed consumption, Kg | 0.84 | 1.01 | 0.78 | 0.83 |
| Body weight gain, Kg | $0.44^a$ | $0.30^b$ | $0.38^{ab}$ | $0.40^a$ |
| Feed Conversion | $1.90^b$ | $3.37^a$ | $2.05^b$ | $2.08^b$ |
| Live performance, 0-28 d | | | | |
| Feed consumption, Kg | 1.21 | 1.31 | 1.19 | 1.24 |
| Body weight gain, Kg | 0.62 | 0.46 | 0.57 | 0.60 |
| Feed Conversion | $1.95^b$ | $2.84^a$ | $2.08^b$ | $2.06^b$ |
| Necrotic enteritis lesion score | $0.0^c$ | $1.1^a$ | $0.3^c$ | $0.6^b$ |

TABLE 24-continued

Summary 2018 SPRG NQ NE0716 Trial

| | Treatment | | | |
|---|---|---|---|---|
| Variable | Non Challenged Control | Challenged Control | BMD | Formulated yeast + *B. licheniformis* |
| Necrotic enteritis related mortality, % | $0^{b}$ | $17^{a}$ | $3^{b}$ | $2^{b}$ |

$^{a,b,c}$Means within a row with no common superscripts differ significantly (P < 0.05)

Example 9: Determine the Effect of Feeding *Capsicum* Product, Antimicrobial Clay and *Bacillus licheniformis* to Broilers Challenged with *C. perfringens*

The study was conducted to evaluate the effects of *Capsicum* Product and Antimicrobial Clay with or without *B. licheniformis* in broilers raised in pens on new litter (Table 25). A total of 1500 day-old male Ross×Ross chicks were obtained from a commercial hatchery. Chicks were vaccinated for Marek's and reovirus at the hatchery.

Experimental Diets

Feed consisted of non-medicated commercial-type broiler starter, grower, and finisher diets compounded according to meet or exceed NRC nutrient guidelines and contained feedstuffs commonly used in the United States (Table 26). Rations were fed ad libitum from date of chick arrival as follows: Starter—DOT 0 until DOT 14, grower DOT 14 to DOT 28 and finisher from DOT 28 to DOT 41 (study termination). Diets were fed as crumbles (starter feed) or pellets (grower and finisher feed). Pelleting of diets (grower and finisher diets) were manufactured with a California Pellet mill (at 80° C.). Experimental treatment feeds were prepared from a basal feed formulation.

Animal Information

Upon arrival all birds were vaccinated (by spray cabinet) with a commercially approved coccidia vaccine at the normal recommended dosage. Only healthy chicks were used in this study.

Housing

Chicks were raised in 5×5 feet (1.5 m×1.5 m) floor pens (stocking density of 1.0 feet$^2$ per bird) in a solid-sided barn, with concrete floors, and under ambient temperature control. At placement, birds were placed on reused litter homogenized from a previous necrotic enteritis study. Each pen contained 1 (one) tube feeder and six (6) nipple drinkers.

Challenge Administration and Sample Collection

1. Necrotic Enteritis Challenge: The challenge model consisted of coccidia from the DOT 0 vaccine and *Clostridium perfringens* (using *Clostridium perfringens* strain #6 [Hofacre, et al., 1998]) combination previously published by Hofacre, et al. (1998).
   A. *Clostridium perfringens* onto feed pans: Treatment feed and water were withdrawn for two (2) to three (3) hours prior to administration of *Clostridium perfringens* #6. A measured amount of water (~125 ml *Clostridium perfringens* #6 to 75 ml water) that was consumed within 30 minutes was used for each pen. The *Clostridium perfringens* #6 fifteen (15) hour culture at ~$1\times10^{8}$ was added to this water and thoroughly mixed and poured into the feed pan of birds in each challenge pen. *Clostridium perfringens* #6 was dosed at ~$1\times10^{8}$ CFU/ml on DOT 20, 21, and 22 to birds in all Treatment Groups.
   B. Coccidia Challenge. Was from cycling of DOT 0 vaccination and spreading *E. maxima* on feeders on DOT 15.
2. Necrotic Enteritis Scoring: DOT 23, three (3) birds per pen were humanely euthanized, weighed necropsied and lesion scored by Dr. Hofacre (Hofacre, 1998).

Lesion score 0=Normal

Lesion score 1=Slight mucus covering small intestine

Lesion score 2=Necrotic small intestine mucosa

Lesion score 3=Sloughed and blood small intestine mucosa and contents

Body and Feed Weight

All birds were weighed by pen on DOT 0, 14, 28, and 41. The trial was terminated on DOT 41. On DOT 14 remaining starter feed was removed, weighed, and replaced with grower feed to DOT 28. On DOT 28 remaining grower feed was removed, weighed back, and replaced with finisher feed to DOT 41 (study termination).

Management

1. All birds were monitored for general flock condition, temperature, lighting, water, feed, litter condition, and unanticipated house conditions/events. Pens were checked daily for mortality. A gross necropsy was performed on all dead or culled birds to determine the bird sex and probable cause of death.

Data was analyzed using one-way ANOVA by the MIXED procedure of SAS for this complete randomized design. Pen served as the experimental unit. The statistical model included pen weight gain, feed consumption, feed conversion, percent NE related mortality and total percent mortality. All results were reported as least squares means. The significance level chosen was $\alpha=0.05$. Treatment effect was considered significant if $P<0.05$, whereas values between $0.05\leq P\leq 0.10$ were considered as statistical trends.

Summary

At 28 days of age birds fed the Antimicrobial Clay+*B. licheniformis* treatment combination and BMD had an increased (P<0.05) body weight gain and decreased (P<0.05) FCR compared to birds fed with no feed additive (Table 27). Broilers fed the combinations of *Capsicum* Product+*B. licheniformis* and Antimicrobial Clay+*B. licheniformis* and BMD had a decreased (P<0.05) FCR compared to the no feed additive control group at 41 days of age. Body weight gain was increased (P<0.05) in birds fed Antimicrobial Clay+*B. licheniformis* and BMD compared to the control fed birds at 41 days of age. Necrotic enteritis lesion score and necrotic enteritis related mortality (Table 28) was numerically reduced in birds fed the *Capsicum* Product+*B. licheniformis,* Antimicrobial Clay+*B. licheniformis* and BMD treatments compared to the no feed additive control fed birds. These results suggest that feeding the combination of *Capsicum* Product+*B. licheniformis,* Antimicrobial Clay+*B. licheniformis* and BMD were effective in controlling *C. perfringens* disease challenge.

TABLE 25

| Experimental treatments | | | | | | |
|---|---|---|---|---|---|---|
| Treatment | Necrotic Enteritis Challenge | Test Product | Starter DOT[1] 0-13 | Grower DOT 14-35 | Finisher DOT 35-41 | # of Pens |
| A | Yes | No Additive | None | None | None | 10 |
| B | Yes | BMD | 50 g/ton | 50 g/ton | 50 g/ton | 10 |
| C | Yes | Capsicum Product | 0.3 lb/ton | 0.3 lb/ton | 0.3 lb/ton | 10 |
| D | Yes | Capsicum Product + *B. licheniformis* | 0.3 lb/ton + $3 \times 10^5$ cfu/g in final feed | 0.3 lb/ton + $3 \times 10^5$ cfu/g in final feed | 0.3 lb/ton + $3 \times 10^5$ cfu/g in final feed | 10 |
| E | Yes | Antimicrobial Clay | 4.0 lb/ton | 4.0 lb/ton | 4.0 lb/ton | 10 |
| F | Yes | Antimicrobial Clay + *B. licheniformis* | 4.0 lb/ton + $3 \times 10^5$ cfu/g in final feed | 4.0 lb/ton + $3 \times 10^5$ cfu/g in final feed | 4.0 lb/ton + $3 \times 10^5$ cfu/g in final feed | 10 |

[1]Day of hatch

TABLE 26

| Composition of the basal diets | | | |
|---|---|---|---|
| Ingredients, Kg/ton | Starter | Grower | Finisher |
| Corn, Yellow Grain | 556.29 | 615.34 | 640.07 |
| Soybean Meal Dehulled, Solvent | 377.55 | 318.36 | 293.02 |
| Fat, Vegetable | 25.55 | 29.11 | 31.1 |
| Dicalcium Phosphate | 20.39 | 18.94 | 17.86 |
| Calcium Carbonate | 10.31 | 9.85 | 9.18 |
| Salt, (NaCl) | 4.61 | 4.39 | 4.41 |
| Methionine, MHA | 3.08 | 2.06 | 2.22 |
| L - LYSINE, 98.5% | 0.82 | 0.70 | 0.89 |
| Trace Mineral Premix | 0.75 | 0.70 | 0.75 |
| Vitamin Premix | 0.65 | 0.50 | 0.50 |
| Total | 1000.00 | 1000.00 | 1000.00 |

TABLE 26-continued

| Composition of the basal diets | | | |
|---|---|---|---|
| Ingredients, Kg/ton | Starter | Grower | Finisher |
| Calculated Nutrients Composition | | | |
| Crude Protein, % | 22.45 | 20.0 | 19.0 |
| Fat, % | 4.85 | 5.35 | 5.61 |
| Crude Fiber, % | 2.19 | 2.12 | 2.10 |
| ME, kcal/Kg | 3054.00 | 3125.00 | 3165.00 |
| Lysine, % | 1.34 | 1.16 | 1.11 |
| Methionine, % | 0.63 | 0.51 | 0.51 |
| Threonine, % | 0.92 | 0.82 | 0.77 |
| Calcium, % | 0.92 | 0.85 | 0.80 |
| Phosphorus, % | 0.45 | 0.71 | 0.68 |
| Phosphorus, Available, % | 0.67 | 0.42 | 0.40 |
| Ca/P Ratio, ratio | 2.04 | 2.02 | 2.00 |
| Sodium, % | 0.21 | 0.20 | 0.20 |

TABLE 27

| Summary 2018 SPRG NQC072018-40 Trial (Example 5) | | | | | | |
|---|---|---|---|---|---|---|
| | Treatment | | | | | |
| Variable | No Feed Additive | BMD | Capsicum Product | Capsicum Product + *B. licheniformis* | Antimicrobial Clay | Antimicrobial Clay + *B. licheniformis* |
| No. of Pens | 10 | 10 | 10 | 10 | 10 | 10 |
| No. of Birds | 250 | 250 | 250 | 250 | 250 | 250 |
| Live performance, 14 d | | | | | | |
| Feed consumption, Kg | 0.44 | 0.44 | 0.45 | 0.43 | 0.48 | 0.47 |
| Body weight gain, Kg | $0.33^{bc}$ | $0.33^{abc}$ | $0.35^{a}$ | $0.32^{c}$ | $0.34^{abc}$ | $0.35^{ab}$ |
| Feed Conversion | $1.35^{ab}$ | $1.35^{ab}$ | $1.30^{b}$ | $1.35^{ab}$ | $1.40^{a}$ | $1.35^{ab}$ |
| Live performance, 28 d | | | | | | |
| Feed consumption, Kg | 1.87 | 1.99 | 1.90 | 1.88 | 1.91 | 1.94 |
| Body weight gain, Kg | $1.15^{c}$ | $1.26^{a}$ | $1.17^{c}$ | $1.18^{bc}$ | $1.15^{c}$ | $1.23^{ab}$ |
| Feed Conversion | $1.63^{ab}$ | $1.58^{c}$ | $1.62^{abc}$ | $1.59^{bc}$ | $1.66^{a}$ | $1.58^{c}$ |
| Live performance, 41 d | | | | | | |
| Feed consumption, Kg | 3.95 | 4.08 | 3.88 | 3.89 | 3.92 | 3.99 |
| Body weight gain, Kg | $2.34^{c}$ | $2.47^{a}$ | $2.34^{c}$ | $2.37^{bc}$ | $2.36^{c}$ | $2.45^{ab}$ |
| Feed Conversion | $1.69^{a}$ | $1.65^{b}$ | $1.66^{ab}$ | $1.64^{b}$ | $1.66^{ab}$ | $1.63^{b}$ |
| Total mortality, % | $6.0^{ab}$ | $4.4^{b}$ | $12.0^{a}$ | $8.4^{ab}$ | $11.6^{a}$ | $8.0^{ab}$ |

$^{a,b,c}$Means within a row with no common superscripts differ significantly ($P < 0.05$)

TABLE 28

2018 SPRG NQC072018-40 Trial (Example 5) Clinica necrotic enteritis

| Treatment | Percent NE Mortality | Average NE Lesion Score |
|---|---|---|
| No Feed Additive | $2.40^{b}$ | 0.53 |
| BMD | $1.20^{b}$ | 0.43 |
| *Capsicum* Product | $7.60^{a}$ | 0.40 |
| *Capsicum* Product + *B. licheniformis* | $1.60^{b}$ | 0.33 |
| Antimicrobial Clay | $4.80^{ab}$ | 0.53 |
| Antimicrobial Clay + *B. licheniformis* | $1.60^{b}$ | 0.50 |

What is claimed is:

1. A method for improving performance of non-human animals, the method comprising feeding the non-human animal a feed composition comprising a basal animal diet supplemented with a direct fed microbial (DFM) and comprising active ingredients selected from i) *Capsicum* product; ii) an antimicrobial clay; iii) formulated yeast; and iv) *Capsicum* product and formulated yeast wherein the improving performance comprises one or more of: an improvement of at least 5% in necrotic enteritis lesion score, an improvement of at least 45% in necrotic enteritis related mortality, or any combination thereof compared to an animal not fed the feed composition;

wherein the DFM is a probiotic or prebiotic living microorganism, wherein the DFM is *Bacillus licheniformis*, and wherein the *Bacillus licheniformis* in the feed composition is at a concentration of about $1\times10^{4}$ cfu/g to about $1\times10^{6}$ cfu/g in the feed composition.

2. The method of claim 1, wherein improving performance further comprises an increase in body weight gain, a decrease in feed conversion rate (FCR), an increase in average daily weight gain (ADG), an increase in average daily food intake (ADFI), or any combination thereof.

3. The method of claim 1, wherein the non-human animal is a chicken, and wherein the feed composition is fed to said chicken at a growth-phase selected from the group consisting of a starter, a grower, and a finisher.

4. The method of claim 1, wherein the feed composition improves necrotic enteritis lesion score by about 5% to about 60%.

5. The method of claim 1, wherein the feed composition is fed to the non-human animal at a growth period of between: i) day 0 and day 14;

ii) day 14 and day 28; iii) day 28 and day 41, or iv) day 0 and day 41.

6. The method of claim 1, wherein the *Bacillus licheniformis* in the feed composition is at a concentration of about $1\times10^{5}$ cfu/g to about $1\times10^{6}$ cfu/g in the feed composition.

7. The method of claim 1, wherein the *Capsicum* product is selected from the group consisting of a capsaicinoid, a vanilloid, *Capsicum*, macerated hot peppers, ground hot peppers, hot pepper extract, capsaicin-containing plant materials, encapsulated ground peppers, a coated capsaicin product, and any combinations thereof.

8. The method of claim 1, wherein the antimicrobial clay is at a concentration of about 2 lb./ton (1 g or 0.1% w/w) to about 6 lb./ton (3 g or 0.3% w/w).

9. The method of claim 1, wherein the feed composition improves necrotic enteritis related mortality by about 65% to about 100%.

10. The method of claim 1, wherein the improving performance comprises an improvement of at least about 10% in necrotic enteritis lesion score.

11. The method of claim 1, wherein the improving performance comprises an improvement of at least about 50% in necrotic enteritis related mortality.

12. A method for improving performance of a non-human animal, the method comprising feeding the non-human animal a feed composition comprising a basal animal diet supplemented with a direct fed microbial (DFM) and comprising active ingredients selected from i) *Capsicum* product; ii) an antimicrobial clay; iii) formulated yeast; and iv) *Capsicum* product and formulated yeast, wherein the improving performance comprises a decrease in feed conversion rate (FCR) of at least 2.79% compared to an animal not fed the feed additive composition, or wherein the improving performance comprises an increase of body weight gain of at least 2.71% compared to an animal not fed the feed additive composition, or wherein the improving performance comprises a reduced mortality of at least 10% compared to an animal not fed the feed additive composition wherein the DFM is a probiotic or prebiotic living microorganism, wherein the DEM is *Bacillus licheniformis*, and wherein the *Bacillus licheniformis* in the feed composition is at a concentration of about $1\times10^{4}$ cfu/g to about $1\times10^{6}$ cfu/g in the feed composition.

13. The method of claim 12, wherein improving performance comprises an increase of body weight gain of at least 2.71% compared to an animal not fed the feed additive composition.

14. The method of claim 12, wherein improving performance comprises a reduced mortality of at least 10% compared to an animal not fed the feed additive composition.

15. The method of claim 12, wherein improving performance comprises a decrease in feed conversion rate (FCR) of at least 2.79% compared to an animal not fed the feed additive composition.

16. The method of claim 12, wherein the non-human animal is a chicken, and wherein the feed composition is fed to the chicken at a growth-phase selected from the group consisting of a starter, a grower, and a finisher.

17. The method of claim 12, wherein the feed composition improves the necrotic enteritis lesion score by about 5% to about 60%.

18. The method of claim 12, wherein the feed composition improves necrotic enteritis related mortality by about 45% to about 100%.

19. The method of claim 12, wherein the feed composition is fed to the non-human animal at a growth period of between: i) day 0 and day 14;

ii) day 14 and day 28; iii) day 28 and day 41, or iv) day 0 and day 41.

* * * * *